(12) United States Patent
Schenkl et al.

(10) Patent No.: US 7,733,097 B2
(45) Date of Patent: Jun. 8, 2010

(54) METHOD FOR DETERMINING A PROPERTY OF A FLUID FOR A HOUSEHOLD DEVICE

(75) Inventors: Johann Schenkl, Bodenwohr (DE); Herbert Altenhofer, Kallmunz (DE)

(73) Assignee: emz-Hanauer GmbH & Co. KGaA, Nabburg (DE)

( * ) Notice: Subject to any disclaimer, the term of this patent is extended or adjusted under 35 U.S.C. 154(b) by 417 days.

(21) Appl. No.: 11/719,329

(22) PCT Filed: Sep. 6, 2005

(86) PCT No.: PCT/EP2005/009563

§ 371 (c)(1),
(2), (4) Date: Jun. 19, 2007

(87) PCT Pub. No.: WO2006/050767

PCT Pub. Date: May 18, 2006

(65) Prior Publication Data

US 2009/0140754 A1 Jun. 4, 2009

(30) Foreign Application Priority Data

Nov. 15, 2004 (DE) .................. 20 2004 017 677 U

(51) Int. Cl.
*G01N 27/04* (2006.01)
(52) U.S. Cl. ..................... 324/693; 324/453

(58) Field of Classification Search .............. 324/693, 324/439, 453, 722
See application file for complete search history.

(56) References Cited

U.S. PATENT DOCUMENTS

| 4,257,708 A | | 3/1981 | Fukuda |
| 4,320,010 A | * | 3/1982 | Tucci et al. .................. 210/662 |
| 5,159,823 A | * | 11/1992 | Fukuda et al. ............. 68/12.21 |
| 5,446,831 A | | 8/1995 | Boyer et al. |
| 2003/0041653 A1 | * | 3/2003 | Matsiev et al. ............. 73/54.25 |

FOREIGN PATENT DOCUMENTS

| DE | 19725536 A1 | 12/1998 |
| DE | 19842644 A1 | 3/2000 |
| DE | 10119932 A1 | 10/2002 |

* cited by examiner

*Primary Examiner*—Vincent Q Nguyen
(74) *Attorney, Agent, or Firm*—Robert R Deleault, Esq.; Mesmer & Deleault, PLLC

(57) ABSTRACT

Method for determining a property of a fluid for a household device includes the following steps: measurement of a physical variable of the fluid associated with the property of the fluid, in each case when a first parameter influencing the physical variable has one of at least two predetermined values, in order to obtain at least two measurement values for the first parameter, and correlation of the at least two measurement values for the first parameter, in order to obtain a first value characterizing the property of the fluid.

4 Claims, 17 Drawing Sheets

METHOD FOR DETERMINING A PROPERTY OF A FLUID FOR A HOUSEHOLD DEVICE

FIELD OF THE INVENTION

The present invention relates in general to properties of fluids and in particular to a method for making statements regarding a property of a fluid that is used or can be used in a household device, by measuring a physical variable.

BACKGROUND OF THE INVENTION

In order to be able to control the operation of household devices reliably and automatically, it is necessary to determine their operating states reliably and accurately. Thus, it is known for example in household devices such as for example washing machines, dishwashers and dryers to monitor the actual properties of fluids that are employed. In the case of washing machines and dishwashers the optical transmission of cleaning liquid is for example measured in order to determine the actual degree of cleanliness of objects to be cleaned and to appropriately control the operation. The same also applies to the drying air used in dryers.

Also, the measurement of fluid temperature and electrical conductivity can provide information on the actual operating state and establish a basis for how the operation should subsequently be controlled, in order for example to achieve an optimum cleaning result.

Known approaches have disadvantages as regards the measurement accuracy and reliability. Thus, for example, measurements can be affected on account of the operation of the household device and the measurement methods that are employed, with the result that the measurement results may be inaccurate and unreliable. Also, time-consuming and complex methods are normally required to evaluate the measurement values.

OBJECT OF THE INVENTION

The object of the invention is to provide a method by means of which more reliable and more accurate statements can be made regarding fluids used for household devices, and which in particular overcomes the disadvantages of the prior art.

BRIEF DESCRIPTION OF THE INVENTION

In order to achieve this object the present invention provides a method according to claim 1, with which a property of a fluid for a household device can be determined.

A preferred use of the method according to the invention comprises the monitoring of fluids (e.g. added fresh water, cleaning fluid, waste water, incoming air, drying air, waste air) that are used or can be used in washing machines, dishwashers and dryers.

In the method according to the invention a physical variable of a fluid is measured, which is connected with the property of the fluid and directly or indirectly enables statements to be made regarding the property to be determined. The physical variable is measured each time a first parameter influencing the physical variable has one of at least two predetermined values, in order to obtain at least two measurement values for the said first parameter.

Examples of the physical variable include individual or a plurality of physical and/or chemical characteristics, the electrical conductivity, the optical transmission, temperature, flow behaviour, absorption, and thermal dissipation and thermal conductivity of the fluid.

In this connection it is envisaged that the physical variable is measured when the first parameter has a first predetermined value, so as to obtain a first measurement value for the first parameter, and when the first parameter has a second predetermined value, so as to obtain a second measurement value for the first parameter, and optionally when the first parameter has a third predetermined value, so as to obtain a third measurement value for the first parameter, etc.

The at least two measurement values for the first parameter are then correlated in order to obtain a first characteristic value for the fluid, which characterises the property of the fluid to be determined.

The individual measurement values may be influenced for example by operating states of the household device, external influences, variables influencing the physical variable itself, which may also include the first parameter, in such a way that no accurate and/or reliable statements can be made regarding the property to be determined. By correlating the at least two measurement values for the first parameter such influences can be avoided and a characteristic value can be obtained which enables more accurate, more reliable and also quicker statements to be made regarding the property of the fluid.

The at least two measurement values can be obtained by using the same measurement arrangement, or identical or different measurement arrangements. This is also envisaged if, as described hereinafter, further parameters are used and/or have to be maintained.

Thus, it is possible for example to determine measurement values with the same electrodes or sensors of a measurement arrangement or to determine at least one measurement value with an electrode or sensor combination of a measurement arrangement, while further measurement values are obtained with another electrode or sensor combination of the measurement arrangement, or electrodes or sensors of another measurement arrangement.

By the use of or on the basis of the first characterising value, statements can be made regarding the property of the fluid and/or an operating state and/or a process variable of the household devices.

It is understood in particular in this connection that, on the basis of the first characterising value, statements can be made regarding not only the property, but also at least to some extent characteristics of the fluid that depend on the said property. Thus, it is envisaged for example that if on the basis of the first characteristic value a statement is made in connection with the electrical conductivity of the fluid, then on the basis of this or in conjunction with a determined electrical conductivity statements are made regarding constituents, substances, etc. present in the fluid (for example the nature and/or amount of an added cleaning fluid or detergent). Another example is the determination of an operating state of the household device on the basis of the temperature or turbidity (optical transmission) of the fluid, which for example enable statements to be made as to how far a heating or cooling cycle has progressed, whether sufficient fresh water or fresh air has been added, or sufficient waste water or waste air has been extracted.

According to one embodiment the at least two measurement values for the first parameter are measured if at the same time at least a second parameter influencing the physical variable has a predetermined first constant value. This embodiment has inter alia the advantage that dependencies of the physical magnitude of two parameters are taken into account.

According to a further embodiment the physical variable is measured each time the first parameter has one of the at least two predetermined values and the second parameter has a predetermined second constant value, so as to obtain at least two further measurement values for the first parameter.

A correlation of the at least two further measurement values for the first parameter enables a second value, characterising the property of the fluid, to be obtained. A second characterising value may also be determined by correlating at least one of the two above measurement values and at least one of the at least two further measurement values for the first parameter.

The steps envisaged in this embodiment may also be carried out as regards predetermined further constant values for the second parameter.

In a further embodiment the physical variable is measured each time a third parameter influencing the physical variable has one of at least two predetermined values, so as to obtain at least two measurement values for the third parameter. A correlation of the at least two measurement values for the third parameter enables a third value, characterising the property of the fluid, to be obtained.

In embodiments in which more than one characterising value is calculated or derived, it is possible on the basis of at least two characterising values (e.g. the first and third characterising value) to make statements regarding the property of the fluid and/or on operating state and/or a process variable of the household device. The relevant comments made above apply here as appropriate.

Measurements of the physical variable may be carried out in a parameter-related manner in succession or substantially at the same time.

With a simultaneous implementation all measurements can be carried out at substantially the same point in time or over a period of time, in which it may be assumed that no time-dependent and/or dynamic effects influence the measurements. A simultaneous implementation is also understood to mean that measurements for a first predetermined value of the first parameter and a first predetermined value of the third parameter are carried out simultaneously, measurements for a second pre-determined value of the first parameter and a second predetermined value of the third parameter are carried out simultaneously, and so on. Also, it is envisaged that two or more measurements can be carried out simultaneously, while the remaining measurements to be carried out take place in a time-staggered manner and/or in succession.

In order to determine a second or further properties of the fluid, it is envisaged to carry out the steps as regards a second or further physical variable or variables according to one of the preceding claims, which permits statements to be made regarding the second property or further properties. This embodiment may be regarded as a "repetition" of the method according to the invention, in which the "repetitions" may be carried out in a time-staggered manner or at least to some extent simultaneously.

In one embodiment, noise occurring at least during the measurement of a physical variable is determined and evaluated. This permits not only a measurement technology evaluation of the corresponding measurement, but in addition noise can provide further information on the fluid and/or the operating state of the household device. For example, noise can provide information on which fraction grease for example is present in the fluid, and/or in which regions of a dishwasher objects being cleaned are located.

The first parameter may comprise one of the following types of parameters:

frequencies, or electrical measurement voltages, or electrical measurement currents, or wave forms of an electrical measurement current or of an electrical measurement voltage, or measurement positions, or measurement paths, or arrangement of sensors, detectors, transmitters and/or electrodes relative to one another, used in the measurement of the physical variable, or arrangement of sensors, detectors, transmitters and/or electrodes relative to the fluid, or sensor, detector, transmitter and/or electrode geometry, or sensor, detector, transmitter and/or electrode material, or characteristics of optical diaphragms, or characteristics of field line diaphragms, or operating states of the household device, or noise occurring in the measurement of the physical variable.

In the parameter type "operating states of the household device" it is for example possible to achieve predetermined parameter values if the household device adopts controllably predetermined operating states. For example, the pump of a washing machine can be operated at full capacity, half capacity or not at all, in order specifically to achieve operating states. The same applies as appropriate to heat-generating components, movable components and components of a household device to which fluids, substances, etc. may be added and/or from which fluids, substances, etc. may be removed.

In order to be able to realise predetermined parameter values in the parameter type "noise occurring in the measurement of the physical variable", it is for example envisaged in the case of a dishwasher to operate in a predetermined manner components by means of which cleaning fluid is distributed in the wash compartment, (e.g. deactivation and/or activation of the upper and/or lower spray arms of a dish-washer).

The first parameter may also denote a combination of the aforementioned parameter types. For example, the first parameter may comprise the parameter type combinations "frequency—measurement voltage", "wave form—measurement path", "characteristics of optical diaphragms—measurement voltage", etc. This optionally also applies to the second and third parameters.

When using the second and/or third parameter it is preferred that the two or three parameters, when they respectively have only one parameter type, differ in their parameter types. In the case of one or more parameter type combinations it is preferred if the two or three parameters differ at least in one parameter type.

According to preferred embodiments the physical variable denotes an electrical conductance, an optical transmission, an optical absorption, an optical scattering and/or a temperature of the fluid.

An electrical conductance is understood in particular to denote the ohmic and/or capacitive conductance or the reciprocal values of the ohmic and/or capacitive resistances of the fluid.

In this connection it is envisaged that the physical variable is measured by using an impedance measurement method, in which impedances between conductance electrodes caused by the fluid are measured, or by using an optical measurement method, in which at least one optical measurement beam propagates through the fluid, or by using a temperature measurement method (e.g. calorimetric method).

As mentioned above, the first parameter may comprise one parameter type of a combination of at least two parameter types. Accordingly, the following embodiments should be understood as not mutually exclusive, but combinable with one another.

The first parameter may denote frequencies of electrical currents, electrical voltages or optical measurement beams employed in the implementation of the measurement method, wherein the first value of the first parameter may denote a first frequency and the second value of the first parameter may denote a second frequency.

The first parameter may denote electrical currents or electrical voltages employed in the implementation of the measurement method, wherein the first value of the first parameter may denote a first electrical current or a first electrical voltage, and the second value of the first parameter may denote a second electrical current or a second electrical voltage.

The first parameter may denote distances between electrodes, detectors, transmitters, optical components or sensors employed in the implementation of the measurement method, wherein the first value of the first parameter may denote a first distance, and the second value of the first parameter may denote a second distance.

The first parameter may denote wave forms of electrical currents, electrical voltage or optical measurement beams used in the implementation of the measurement method, wherein the first value of the first parameter may denote a first wave form and the second value of the first parameter may denote a second wave form.

The first parameter may denote field line diaphragm geometries effective for electromagnetic fields in embodiments in which impedance measurements are carried out, wherein the first value of the first parameter may denote a first field line diaphragm geometry and the second value of the first parameter may denote a second field line diaphragm geometry.

The first parameter may denote intensities of optical measurement beams in embodiments in which optical measurement beams are used, wherein the first value of the first parameter may denote a first intensity and the second value of the first parameter may denote a second intensity.

The first parameter may denote diaphragm geometries effective for optical measurement beams in embodiments in which optical measurement beams are used, wherein the first value of the first parameter may denote a first diaphragm geometry and the second value of the first parameter may denote a second diaphragm geometry.

The first parameter may denote thermal couplings of the fluid and of a temperature sensor employed in the implementation of the temperature measurement method, in embodiments in which temperature measurements are used, wherein the first value of the first parameter may denote a first thermal coupling of the fluid and of a first temperature sensor, and the second value of the first parameter may denote a second thermal coupling of the fluid and of a second temperature sensor.

The first parameter may denote thermal couplings of temperature sensors in embodiments in which temperature measurements are used, wherein the first value of the first parameter may denote a first thermal coupling of the temperature sensors and the second value of the first parameter may denote a second thermal coupling of the temperature sensors.

If more than two parameters are used, then it is envisaged that, depending on the embodiment and the number of employed parameters, the second parameter is of a parameter type that differs from the parameter type of the first parameter, or the third parameter is of a parameter type that differs from the parameter type of the first parameter, or the second parameter is of a parameter type that differs from the parameter type of the first parameter, and the third parameter is of a parameter type that differs from the parameter type of the first parameter as well as from the parameter type of the second parameter.

BRIEF DESCRIPTION OF THE FIGURES

In the following description of preferred embodiments reference is made to the accompanying drawings, in which.

DESCRIPTION OF PREFERRED EMBODIMENTS

Common to the embodiments described hereinafter is that measurements are made of a physical variable which can influence or affect a property of a fluid to be monitored, which are measured as a function of a first parameter, wherein the physical variables is determined for different parameter values. Also common to the embodiments is that measurements are made of the physical variable as a function of the first parameter, when a second parameter has at least one constant value. With some embodiments measurements of the physical variable are also made when the second parameter has a second, different constant value.

Measurement values of the physical variable with variation of the first parameter, which are produced when the second parameter has a first constant value and, possibly, a second constant value, are used on the one hand in order to obtain information on or to characterise the property of a fluid to be monitored. In addition the measurement results themselves and/or statements resulting therefrom concerning the fluid are used in order to make statements regarding operating states and/or process variables of a household device using the fluid.

In the following description devices, measurement arrangements and components themselves which are designed and constructed for carrying out the invention are first of all described.

Following this preferred embodiments of the method according to the invention are discussed separately according to physical variables and separately according to parameters. A simultaneous implementation in the sense described in the introduction, apart from allowing statements hereinafter dependent on the implementation, also allows statements to be made regarding a fluid to be monitored, which in particular take into account interactions between physical variables.

Figure 1:
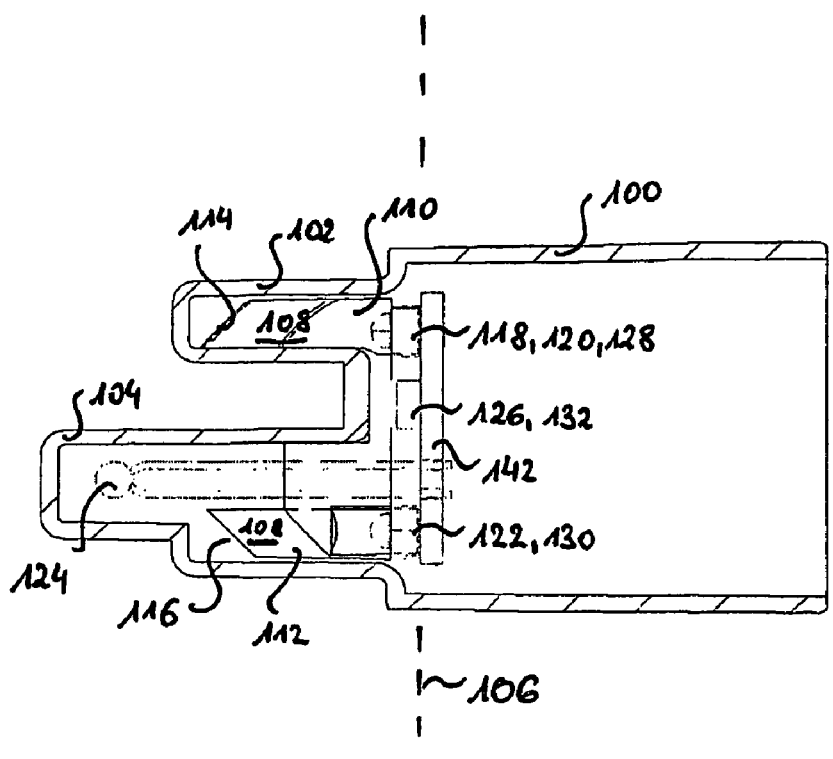
FIGS. 1 and 2 are diagrammatic representations of a device for carrying out the pre-sent invention.
Figure 2:
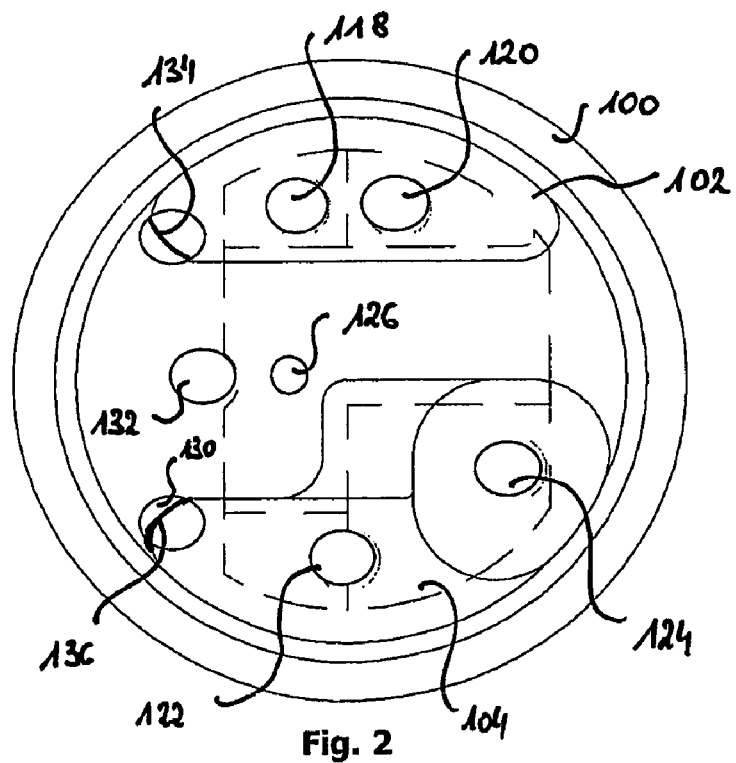

The device illustrated diagrammatically in cross-sectional views in FIGS. 1 and 2 enables a plurality of physical variables of a fluid to be determined, and permits the implementation of various embodiments. The device comprises a housing 100 with a first housing finger 102 and a second housing finger 104. With respect to a plane 106 denoted as a base plane, the second housing finger 104 extends further from the base 106 than the first housing finger 102. In the assembled state this means that the second housing finger 104 projects further into a fluid to be measured.

The housing 100 may be made as a whole of a transparent material, for example of glass and/or plastics. The housing 100 is transparent at least in the regions of the housing fingers 102 and 104, from which an optical measurement beam from the housing 100 is to exit or enter.

A light-conducting body 108 is arranged in the housing 100, which body comprises a first light-conducting body finger 110 and a second light-conducting body finger 112. The first and second light-conducting body fingers 110 and 112 extend into the first and second housing fingers 102 and 104. The light-conducting body 108 is preferably formed in one piece. It is however also possible to form the light-conducting body 108 in two pieces, in which case it is then possible to restrict the light-conducting body 108 basically to the first and second light-conducting body fingers 110 and 112.

The light-conducting body fingers 110 and 112 include reflecting surfaces 114 and 116 at their ends facing towards the free ends of the housing fingers 102 and 104. The reflecting surfaces 114 and 116 serve for the internal reflection of the measurement beam in the light-conducting body fingers 110 and 112, i.e. for the reflection of the optical measurement beam within the light-conducting bodies 110 and 112.

A first and a second receiver for the optical measurement beam are arranged adjacent to the end of the light-conducting body finger 110 facing opposite the reflecting surface 114, in such a way that light reflected at the reflecting surface 114 can reach the first and second receivers 118 and 120.

A transmitter 122 for the optical measurement beam is arranged adjacent to the end of the second light-conducting body finger 112 facing opposite the reflecting surface 116, so that the measurement beam emitted by the transmitter 122 can propagate through the second light-conducting body finger 112 and can be reflected at the reflecting surface 116.

The configuration of the light-conducting body 108 (in particular the reflecting surfaces 114 and 116) as well as the arrangement of the first and second receivers 118 and 120 and the transmitter 122 relative to the light-conducting body 108 (in particular to the reflecting surfaces 114 and 116) is such that the optical measurement beam emitted by the transmitter 122 passes through the second light-conducting body finger 112 to the reflecting surface 116, where it is reflected, and is such that the measurement beam exits from the second housing finger 104, propagates through fluid present between the first and second housing fingers 102 and 104, enters the first housing finger 102 for reflection at the reflecting surface 114, and from there is reflected by the first light-conducting body finger 110 to the first and second receivers 118 and 120.

In particular the light-conducting body 108 is configured so that on the one hand a beam path can be realised from the transmitter 122 to the first receiver 118, and on the other hand a beam path can be realised from the transmitter 122 to the second receiver 120. This may be achieved for example by a configuration of the reflecting surface 114 and/or of the reflecting surface 116 in such a way that not only reflection, but also further interactions (e.g. beam splitting, focussing) of the measurement beam with the surface/surfaces 114 and 116 take place there, so that desired beam paths can be achieved.

The transmitter 122, the first and second receivers 118 and 120, and the light-conducting body 108 form part of a device for detecting the optical transmission of the fluid.

A first temperature sensor 124 is arranged in the region of the second housing finger 104 adjacent to its free end. On account of the longer length of the second housing finger 104 compared to the first housing finger 102, the temperature sensor 124 in the installed state of the illustrated device is remote from further components that can generate waste heat falsifying the temperature measurements, and is arranged projecting "far" into fluid to be measured. A second temperature sensor 128 is arranged in the plane of the base 106.

In addition, a first conductance electrode 128, a second conductance electrode 130 and a further, third conductance electrode 132 are present for determining electrical conductances. The first and second conductance electrodes 128 and 130 are designed as oblong electrodes of round cross-section, which extend leftwards with respect to the base plane 106 according to FIG. 1.

Independently of the extent to which the first and second conductance electrodes 128 and 130 are to be brought into contact with fluid to be measured, the first and second housing fingers 102 and 104 comprise longitudinal interruptions (slits) 134 and 136. In the assembled state corresponding regions of the conductance electrodes 128 and 130 extend through the interruptions 134 and 136 into the fluid. In order to prevent a penetration of fluid into the housing 100, the interruptions 134 and 136 and the first and second conductance electrodes 128 and 130 are dimensioned so that they engage one another in a sealing, interlocking and advantageously also frictional manner. In addition or alternatively, the first and second conductance electrodes 128 and 130 may be bonded in the interruptions 134 and 136 or secured in some other way in a sealing-type manner.

The third conductance electrode 132 extends in a region between the first and second housing fingers 102 and 104 from the housing 100.

Figure 3:
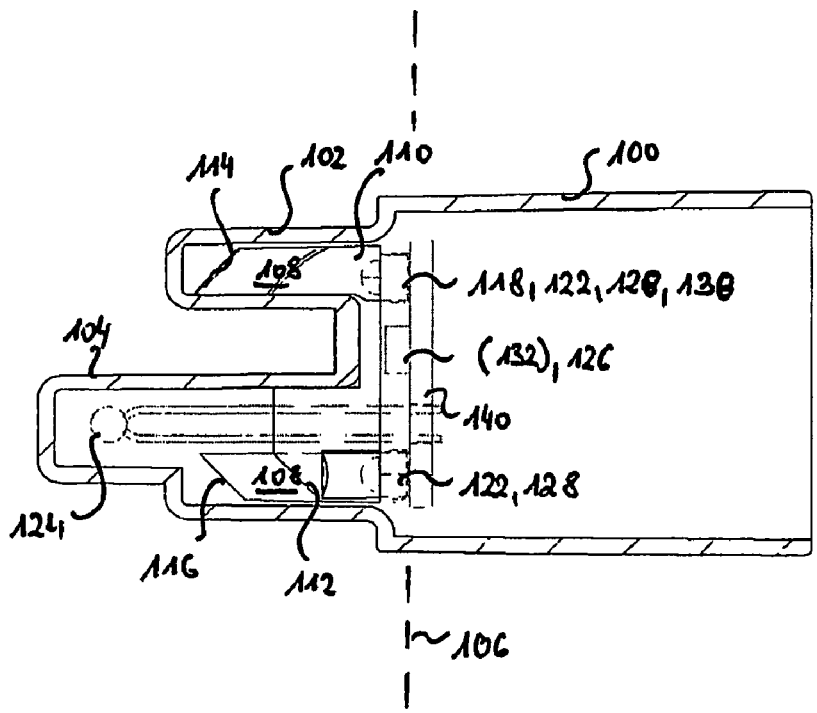
FIGS. 3 and 4 are diagrammatic representations of a further device for carrying out the present invention.
Figure 4:
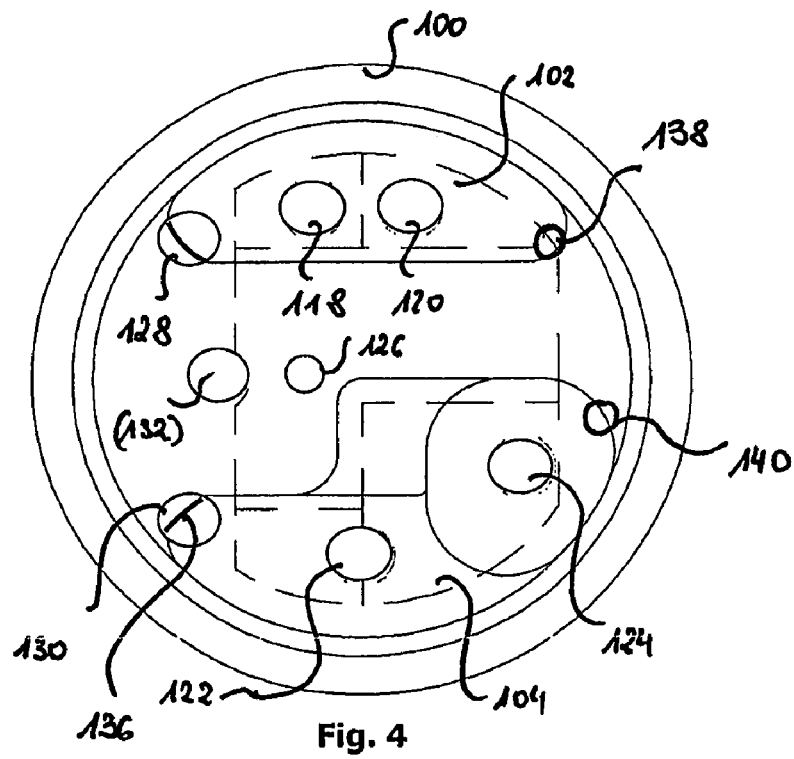

The device illustrated in FIGS. 3 and 4 differs from the device according to FIGS. 1 and 2 in that the third conductance electrode 132 is omitted, and fourth and fifth conductance electrodes 138 and 140 are provided. The above description regarding the first and second conductance electrodes 128 and 130 applies correspondingly to the fourth and fifth conductance electrodes 138 and 140.

In a device variant (not shown), which may be regarded as a combination of the devices according to FIGS. 1/2 and FIGS. 3/4, the first to fifth conductance electrodes 128, 130, 132, 138 and 140 are provided.

A printed circuit board 142 is used, to which are fixed the transmitters 118, 120, the receiver 122, using corresponding conductor structures, the temperature sensor 124, the temperature sensor 126, and the conductance electrodes. The printed circuit board 142 may also serve for the securement of the light-conducting body 108. In this way a prefabricated and advantageously complete unit can be produced, which for purposes of assembly can be incorporated in a simple way into the housing 100 without the need for further measures, such as for example wiring.

It is intended to use devices designed as "free-standing" sensor units. In this connection control and evaluation devices may be integrated into the housing 100, which on the one hand control the operation and on the other hand evaluate signals provided by various components, so as to provide information from measurements. As an example, the electrical conductance, the optical transmission and the temperature of a fluid may be output by signal technology in this way.

Devices comprising such control and evaluation units are illustrated in FIGS. 5 to 8, in which circumstances or components already discussed there with reference to previous figures and hereinafter also no longer described, are in some cases no longer provided with reference numerals.

Figure 5:
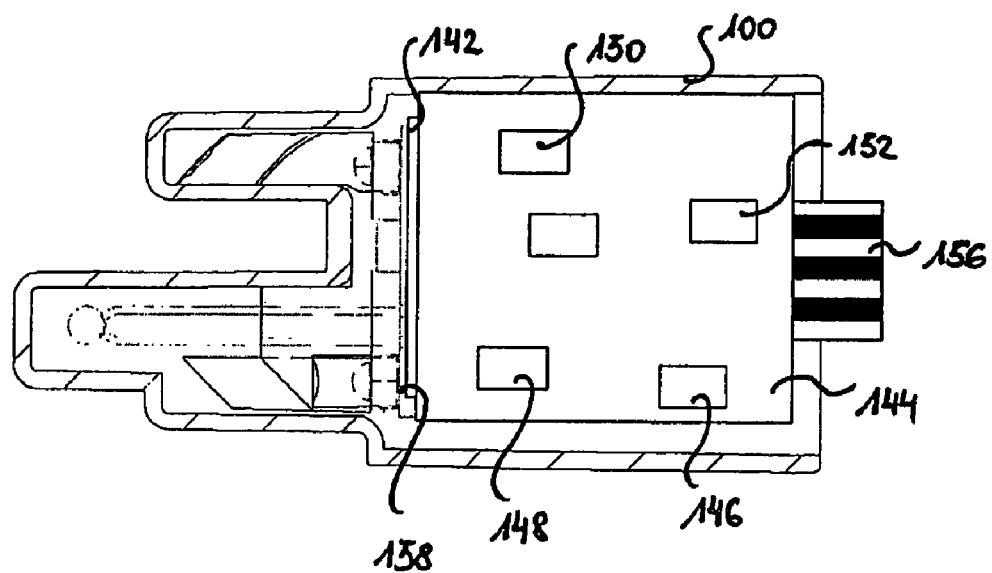
FIGS. 5 and 6 are diagrammatic representations of a further device for carrying out the present invention.
Figure 6:
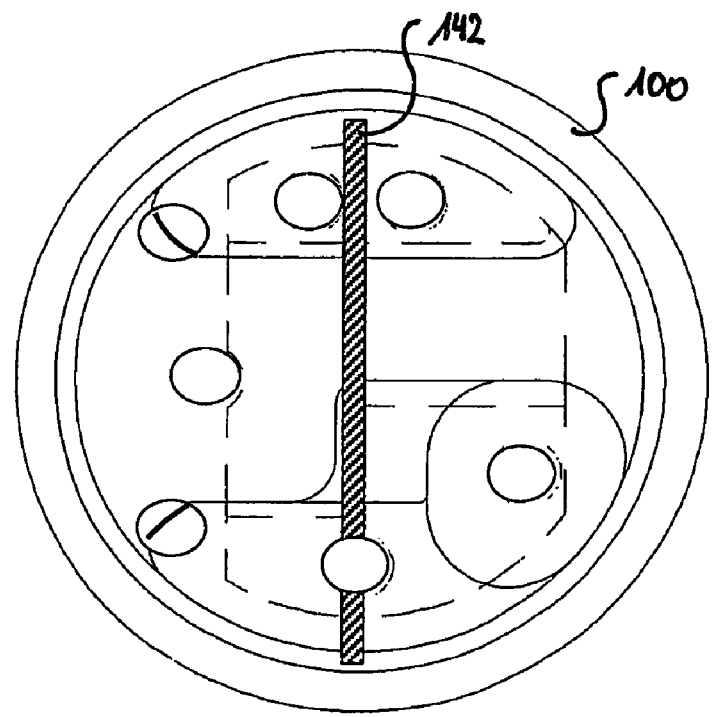

According to FIGS. 5 and 6, in addition to the printed circuit board 142 a further printed circuit board 144 with components 146 to 154 arranged thereon is arranged in the housing. The printed circuit board 144 has at its right-hand end in FIG. 5 a printed circuit board plug 156 for connection for example to a washing machine or rinsing machine; instead of a printed circuit board plug the connection 156 can also be designed as a bus connection, as a combination of electrical and optical connections, soldered connections or spring contacts.

A connection identified by the reference numeral 158 in FIG. 5 is provided for connecting up the printed circuit board 144 and in particular the components 146 to 154 arranged thereon. The connection 158 may also be realised by soldered points, plug-and-socket connections, bus connections, a combination of electrical and optical connections, spring contacts and the like.

Figure 7:
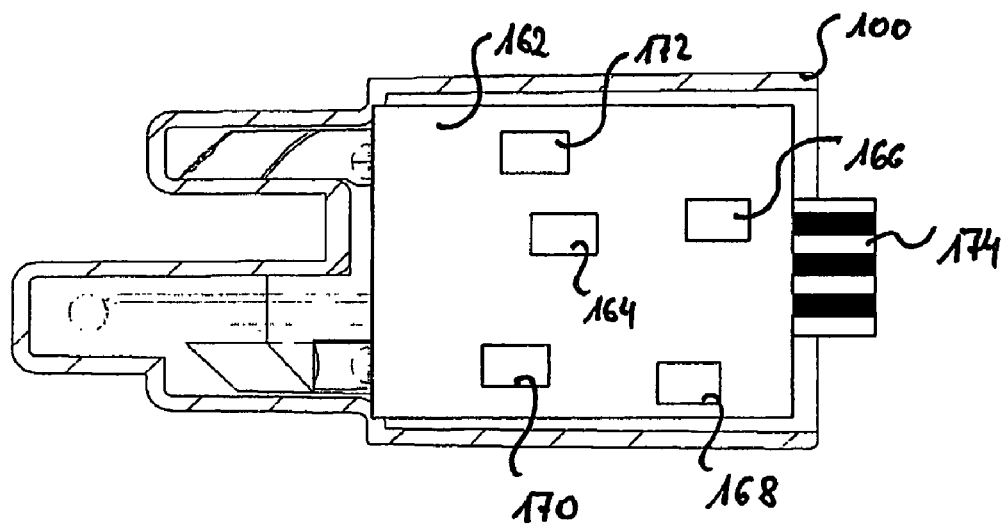
FIGS. 7 and 8 are diagrammatic representations of a further device for carrying out the present invention.
Figure 8:
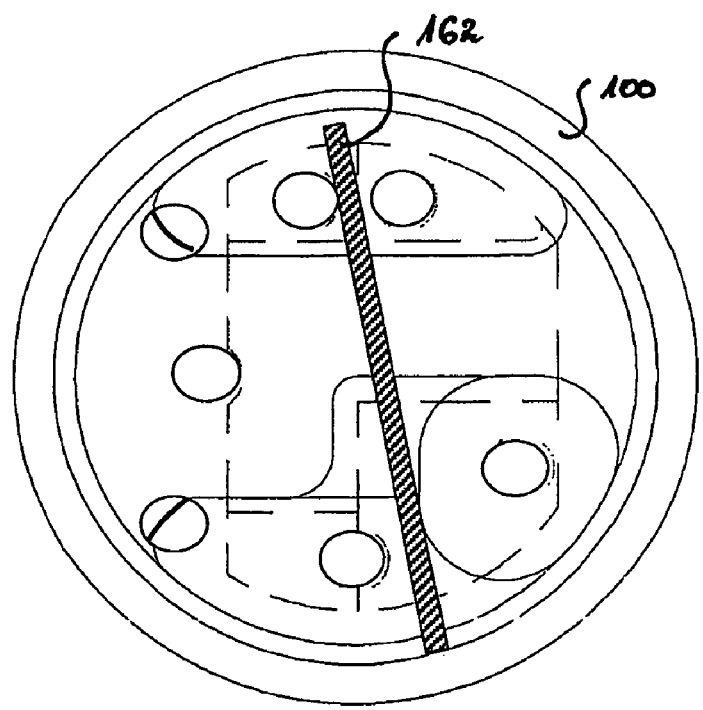

According to FIGS. 7 and 8 only one printed circuit board 162 with components 164 to 172 arranged thereon is used. The above descriptions regarding the printed circuit board plug 156 apply correspondingly to a printed circuit board plug 174 provided on the printed circuit board 162.

Further components in the housing, for example electrical conductance sensors, optical transmitters, optical receivers and temperature sensors may be fixed to the housing 100 and connected via electrically conducting leads (e.g. wired connections, conductive plastics) to the printed circuit board 162.

Figure 9:
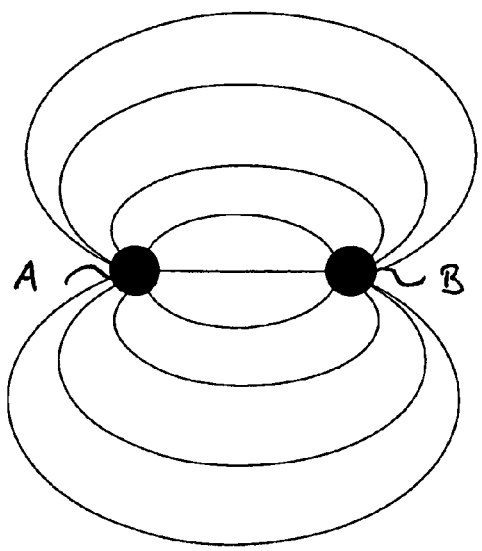
FIGS. 9 and 10 are a diagrammatic representation of a conventional arrangement of conductance electrodes for the conductance measurement.
Figure 10:
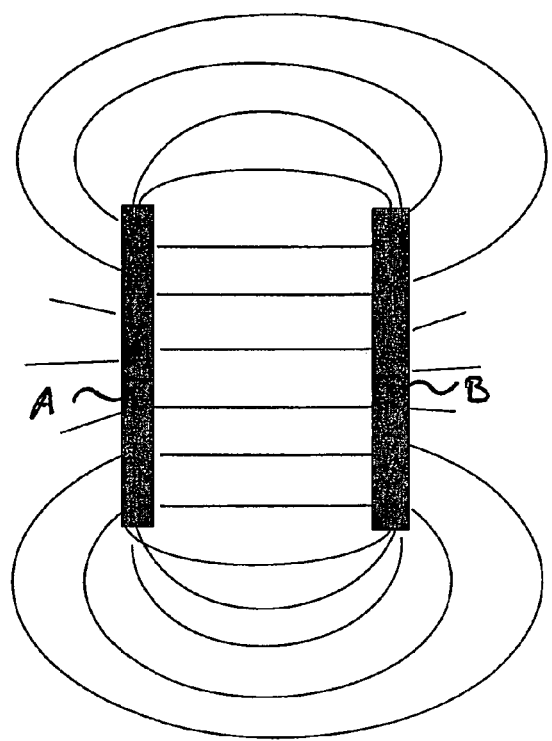

FIGS. 9 and 10 illustrate diagrammatically two conductance electrodes A and B and an electrical field line distribution generated between the conductance electrodes A and B in the measurement mode in a fluid to be measured, when the conductance electrodes A and B, as illustrated in FIGS. 9 and 10, are used in a conventional way arranged extending from a common base freely into the fluid. Problems occurring on account of the field line distribution illustrated in FIGS. 9 and 10 when calculating the electrical conductance or carrying out an approximate calculation are prevented by field line diaphragm devices associated with the conductance electrodes.

Figure 11:
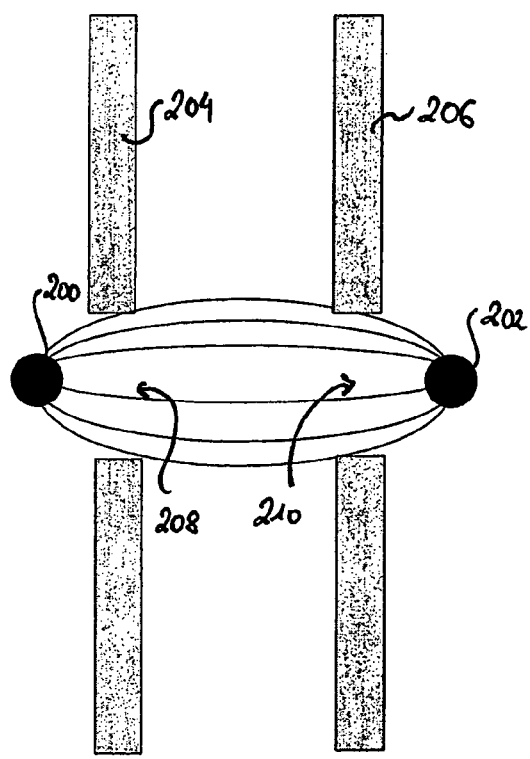
FIGS. 11 and 12 are diagrammatic representations of an arrangement of conductance electrodes for carrying out a preferred embodiment of the present invention for determining the conductance.
Figure 12:
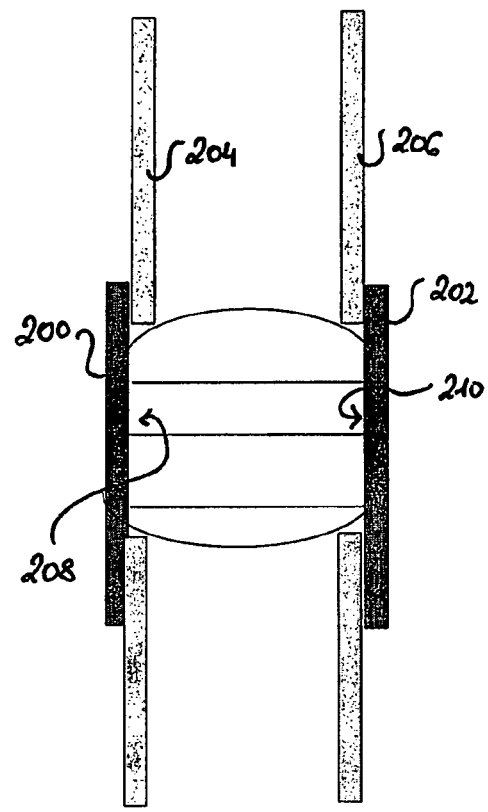

FIGS. 11 and 12 illustrate an arrangement of two conductance electrodes 200 and 202 and two field line diaphragm devices 204 and 206. The field line diaphragm devices 204 and 206 are made of an electrically insulating, electrically non-conducting material, such as for example glass, plastics, ceramics and the like. Pre-ferred are electrically non-conducting materials that are chemically resistant, temperature insensitive and hydrophobic, so as to prevent completely or keep to a minimum the absorption of fluid, in particular water. Furthermore materials are preferred whose surface state at least partly prevents accumulations and deposits of dust particles, small objects and the like.

The field line diaphragm devices 204 and 206 include respectively an interruption 208 and 210. The interruptions 208 and 210 are formed as oblong, rectangular slits. Accordingly the field line diaphragm devices 204 and 206 may as regards their design be compared to optical slit diaphragms.

The use of the field line diaphragm devices 204 and 206 leads to the field line distribution, illustrated in FIGS. 11 and 12, between the conductance electrodes 200 and 202 when used in a fluid. The field lines extend between the conductance electrodes 200 and 202 in a region situated substantially only between these electrodes. The current flow thereby generated between the conductance electrodes 200 and 202 by the fluid correspondingly occurs substantially only in this region.

By for example reducing the dimensions illustrated in FIG. 11 of the interruptions 208 and 210, a field line propagation between the conductance electrodes 200 and 202 that is substantially rectilinear as regards FIG. 11 can be obtained. Corresponding comments apply as regards the dimensions illustrated in FIG. 12 of the interruptions 208 and 210.

The field line diaphragm devices 204 and 206 "concentrate" the current flow through the liquid to a region lying between the conductance electrodes 200 and 202. The measurement of the conductance of the fluid is thereby simplified. Furthermore, on account of the constricted, concentrated field line distribution, interfering influences on conductance measurements, for example due to neighbouring electrically conducting and/or magnetically conducting materials, are avoided.

Figure 13:
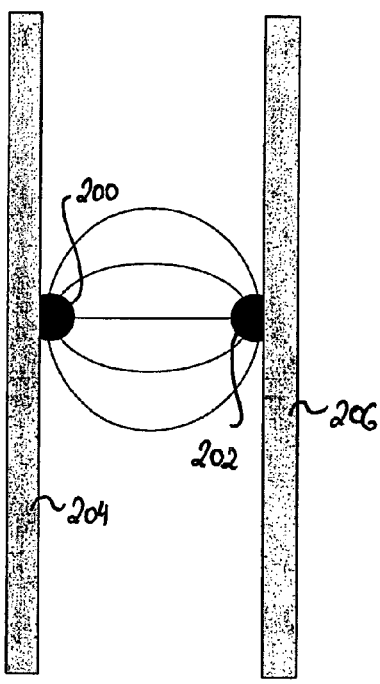
FIGS. 13 and 14 are diagrammatic representations of a further arrangement of conductance electrodes for carrying out a preferred embodiment of the present invention for determining the conductance.
Figure 14:
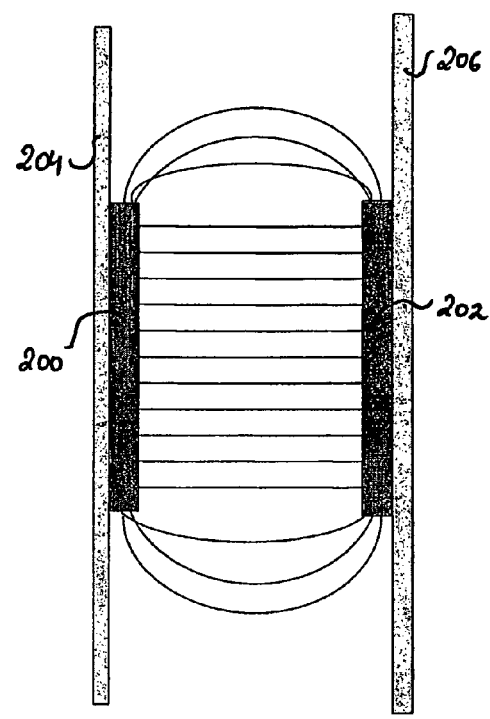

The arrangement illustrated in FIGS. 13 and 14 is comparable to that of FIGS. 11 and 12, apart from the fact that the field line diaphragm devices 204 and 206 do not include any interruptions. Instead, in this embodiment the conductance electrodes 200 and 202 are arranged on the conductance diaphragm devices 204 and 206, for example by thermal connection, pressing or bonding.

As an alternative to the arrangement of the conductance electrodes 200 and 202 on the conductance diaphragm devices 204 and 206 according to FIGS. 13 and 14, the conductance electrodes 200 and 202 may also be embedded in the field line diaphragm devices 204 and 206 so that basically only surfaces of the conductance electrodes 200 and 202 facing opposite one another are left free. A comparable result can be achieved if, in the embodiment of FIGS. 11 and 12, the interruptions 208 and 210 and the conductance electrodes 200 and 202 are dimensioned and arranged in such a way that the interruptions 208 and 210 enclose or frame the conductance electrodes 200 and 202.

Figure 15:
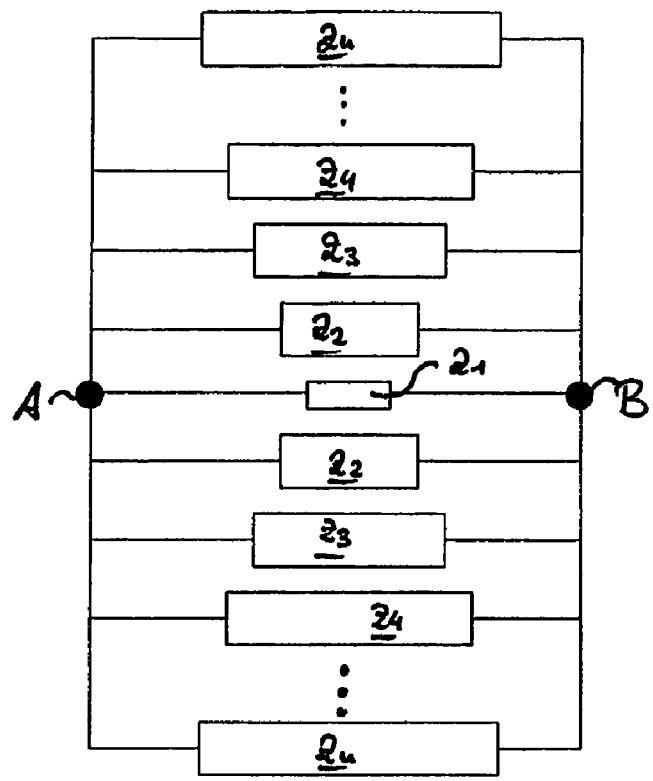
FIG. 15 is an illustrative substitute connection diagram for the arrangement of FIGS. 9 and 10.
Figure 16:
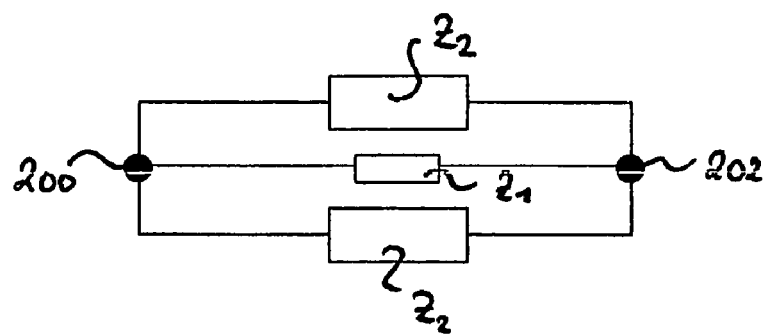
FIG. 16 is an illustrative substitute connection diagram for the arrangement of FIGS. 11 and 12 and FIGS. 13 and 14, FIGS. 17 and 18 are illustrative substitute connection diagrams with regard to conductance measurements of possible leakage paths.

For a further explanation of the arrangements according to FIGS. 11/12 and 13/14 compared to the arrangement according to FIGS. 9/10, reference is made to FIGS. 15 and 16, which show illustrative substitute circuit diagrams for these arrangements.

FIG. 15 illustrates in a simplified manner impedances, effective between the conductance electrodes A and B, of fluid located between these electrodes. For electric current propagating "directly, rectilinearly" through the fluid between the conductance electrodes A and B, the relatively smallest impedance $Z_1$ is effective. This current is attributed to field lines propagating "directly, rectilinearly" between the conductance electrodes A and B. For currents which are based on field lines deviating therefrom and which travel a larger distance through the fluid, larger fluid impedances $Z_2$, $Z_3$, . . . $Z_n$ are effective. In this connection the effective impedances are larger the longer the current path; with reference to FIG. 7 this means that for the current attributable to the uppermost field line in FIG. 7, the impedance is larger than for the current attributed to the field line lying thereunder.

FIG. 16 shows in a simplified manner impedance relationships between the electrodes 200 and 202. On account of the field line diaphragm devices 204 and 206 field lines, as illustrated in FIGS. 9 and 10, are restricted to smaller regions compared to FIGS. 7 and 8. This is illustrated in FIG. 16, in that there impedances for "filtered-out" field lines (e.g. $Z_3$, . . . $Z_n$) not present in the arrangements of FIGS. 9 and 10, are not shown. As a result the arrangements of FIGS. 9 to 14 produce an increase in the resistance that overall is effective for conductance measurements between the conductance electrodes 200 and 202, referred to a conductance assumed to be constant. This also means that, compared to the arrangement of FIGS. 7 and 8, changes in conductance (such as for example partial changes in conductance in the region of the conductance electrodes) result in relatively larger changes of the current flowing between the conductance electrodes 200 and 202. Conductance measurements may thus be carried out more accurately and with a higher resolution.

In addition, with the arrangements according to FIGS. 9 to 14 no or relatively fewer "external fluid impedances" play a role. These "external fluid impedances" may adversely affect conductance measurements since corresponding field lines propagate at a larger distance to the conductance electrodes and can lead to erroneous measurements on account of interactions with electrically and/or magnetically conducting materials.

The figures described hereinafter illustrate diagrammatically embodiments that are designed as a sensor unit for a washing machine or a dishwasher.

In order to avoid or reduce the influence of leakage paths that can affect the conductance measurements, the following solutions are provided, which can be used individually and in combination.

Figure 17:
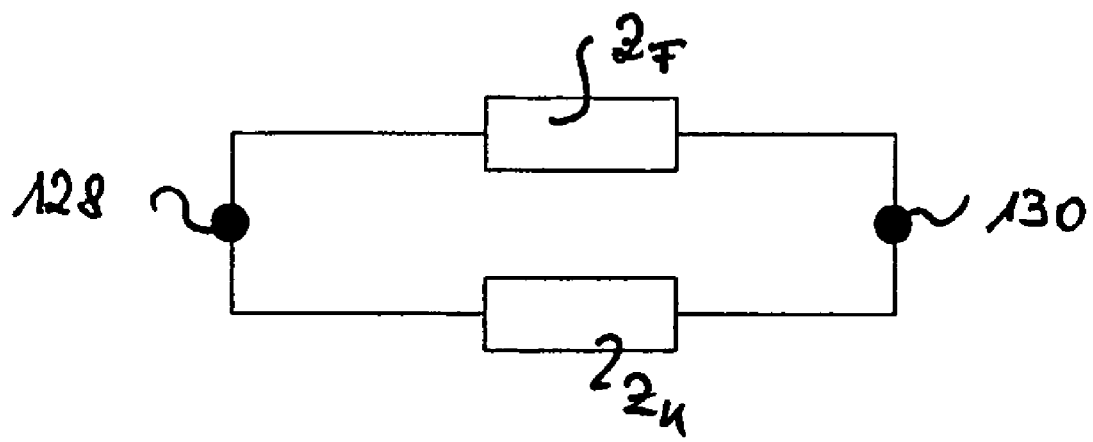

FIG. 17 shows an illustrative substitute circuit diagram for impedance relationships prevailing between two conductance electrodes, in this case the conductance electrodes 128 and 130. The impedance $Z_K$ denotes the impedance of a leakage path, for example over surface regions of the housing 100 between the conductance electrodes 128 and 130. The impedance $Z_F$ denotes the overall effective impedance of fluid between the electrodes 128 and 130. In order to reduce the influence of leakage paths, the ratio of the impedances $Z_K$ and $Z_F$ should be modified so that the proportion of the impedance that is more significant for conductance measurements is provided by the fluid impedance.

This can be achieved by increasing the impedance $Z_K$. An increase of the impedance $Z_K$ leads to a relatively larger current through the impedance $Z_F$. This overall current enables more accurate statements to be made regarding the conductance of the fluid. On account of the increase in the proportion of the current due to the impedance $Z_F$ and a corresponding reduction of the proportion of the current due to the impedance $Z_K$, the proportion of the current flowing as a whole between the conductance electrodes 128 and 130, which is provided by statements regarding the current allowing the conductance, is increased. Influences due to current produced by leakage paths are on the other hand reduced.

The increase in the impedance $Z_K$ may be achieved by electrically insulating jackets, sheathings or coatings on the conductance electrodes 128 and 130. Although reference has hitherto been made in this connection to the conductance electrodes 128 and 130, it is envisaged especially in the case of the third conductance electrode 132 to provide this with such a jacket, sheathing or coating so that basically only its free end or a region adjacent thereto can come into contact with fluid. In the case of the first and second conductance electrodes 128 and 130 this may also be achieved if the interruptions 134 and 136 are configured so that small regions (e.g. ends, lateral surfaces) of the conductance electrodes 128, 130 can (partly) come into contact with fluid.

Furthermore it is possible to increase the impedance $I_K$ by extending surface regions between conductance electrodes on which leakage paths may form. This can be achieved for example if corresponding surface regions of the housing 100 are provided with grooves, corrugations, channels or depressions.

Figure 18:
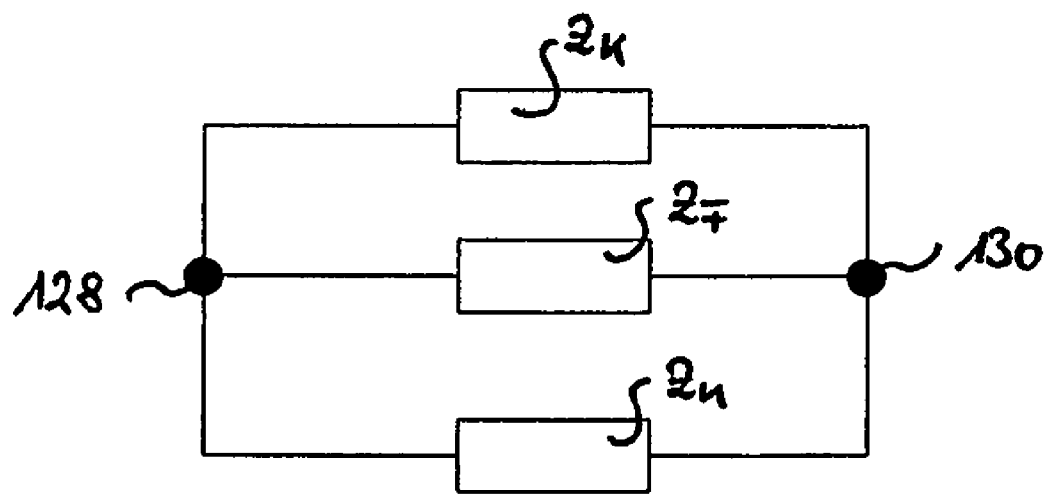

The influence of leakage paths may also at least be reduced if the conductance electrodes are lengthened. This procedure is illustrated by the substitute circuit diagram of FIG. 18. If the conductance electrodes 128 and 130 are lengthened compared to the conductance electrodes according to FIG. 17, for example are designed to be twice as long, the impedance that is as a whole effective on account of the fluid between the conductance electrodes 128 and 130 is reduced, for example is halved. This is attributed to the fact that the current flowing through the fluid between the conductance electrodes 128 and 130 is increased, whereas the current through the impedance $Z_K$ is reduced. The result is a change in the ratio of the fluid to leakage path resistances, described with reference to FIG. 17. Accordingly with this procedure too influences due to leakage paths between the conductance electrodes 128 and 130 are reduced. It should be borne in mind in this connection that a less concentrated, broader field line distribution is produced compared with the previous procedure. Accordingly, with this procedure care should be taken to ensure that when it is employed, the advantages achieved by the use of field line diaphragm devices are not compensated in an unacceptable manner.

As an alternative to the arrangement and configuration of the first and second conductance electrodes 128 and 130 and the interruptions 134 and 136 described above, it is possible to provide the first and second housing fingers 102 and 104 at their free ends with interruptions that are for example round in cross-section, through which the first and second conductance electrodes 128 and 130 can extend into the fluid.

Preferred embodiments with regard to the use of three or more conductance electrodes are discussed with reference to FIGS. 19 to 23.

The distance between two conductance electrodes divided by the exit surface defines a so-called cell constant, in which connection the metallic contact surface of a conductance electrode with fluid may be regarded as the exit surface. Depending on conductance measurement regions, specific cell constants are recommended. The use of more than two conductance electrodes that are arranged at different distances permits a plurality of cell constants that are optimised on different conductance regions. This is possible with three or more conductance electrodes in the case of the embodiments described above.

More than two conductance electrodes arranged at different distances may be operated at the same operating voltage. Higher field strengths and higher currents are thereby generated between conductance electrodes with smaller interspacing. Thus, for example, in the embodiment of FIGS. 3 and 4 the conductance electrodes 128 and 130 and the conductance electrodes 128 and 130 can be operated at the same operating voltage, and thus permit measurement statements regarding two differently long measurement paths. In this connection it is possible to carry out the measurements with the conductance electrodes 128 and 130 and with the conductance electrodes 138 and 140 simultaneously or, in order to avoid interactions between the two measurement fields, intermittently.

Also, it is possible with this arrangement to generate virtually identical fields, which however extend over differently large measurement paths. Measurements carried out in this way enable influences falsifying conductance measurements, such as for example accumulations and/or deposits on conductance electrodes, to be determined at least approximately and, with the appropriate correction, more accurate information on electrical conductances to be obtained.

The arrangement of four conductance electrodes in such a way that in each case two conductance electrodes are arranged adjacent to one another and are at the same distance from the other pair of conductance electrodes, enables an optimal cell constant for the respective conductance measurement region to be adjusted by parallel connection of one or both pairs of conductance electrodes.

Figure 19:
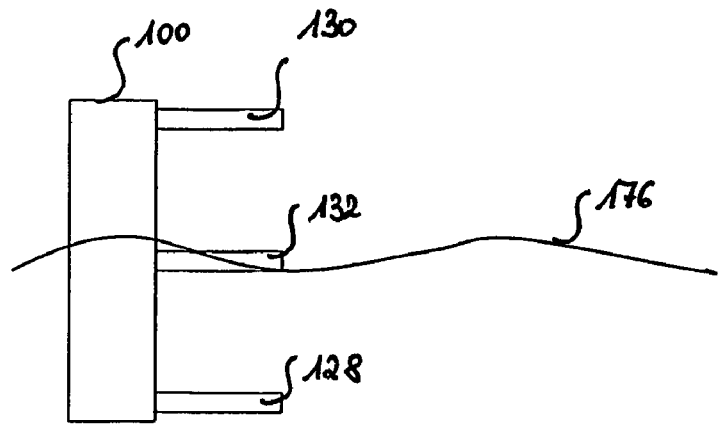
FIG. 19 is a diagrammatic representation intended to illustrate the implementation of a preferred embodiment of the present invention for determining the conductance.

By suitably choosing the orientation of a conductance electrode arrangement when installed for example in a washing machine or rinsing machine, the degree of filling or the level of fluid can be determined by means of the conductance electrodes. If for example the embodiment of FIGS. 1 and 2 as illustrated in FIG. 19 is installed, the conductance electrodes 128, 132 and 130 permit a measurement of the fluid level 174. According to FIG. 19 it is possible to determine whether the fluid level 174 is below the conductance electrode 126, between the conductance electrodes 128 and 132, between the conductance electrodes 132 and 130, or is above the conductance electrode 130. The same applies as appropriate to arrangements with four or more conductance electrodes.

With an arrangement of conductance electrodes that achieves variously long measurement paths, chemical effects, interactions and/or processes which can take place in the vicinity of the conductance electrode, for example depending on the frequency and/or voltage, and which can influence conductance measurements, can be determined.

For example, with the embodiment of FIGS. 3 and 4 variously long measurement paths are obtained for the conductance electrodes 128 and 132 and the conductance electrodes 128 and 130. Assuming that the measurement path between the conductance electrodes 128 and 132 is half as long as the measurement path between the conductance electrodes 128 and 130, the impedance relationships illustrated in FIGS. 20 and 21 are obtained.

Impedances caused by chemical effects, etc. at the conductance electrodes 128, 132 and 130 are denoted in each case in abbreviated form by the impedances $Z_{CH1}$, $Z_{CH2}$ and $Z_{CH3}$.

The impedance that is effective for the conductance electrodes 128 and 132 on account of the fluid is denoted by the impedance $Z_F$. On the basis of the measurement path ratio assumed here, twice as large an impedance is effective between the conductance electrodes 128 and 130 on account of the fluid; this is denoted in FIG. 21 by the two impedances $Z_F$. If, as is assumed here, a symmetrical alternating voltage is applied to the conductance electrodes 128 and 130 and the conductance electrodes 128 and 130 are made of the same material and have the same dimensions, then it may be assumed that the impedances $Z_{CH1}$, $Z_{CH2}$ and $Z_{CH3}$ are equally large.

Figure 20:
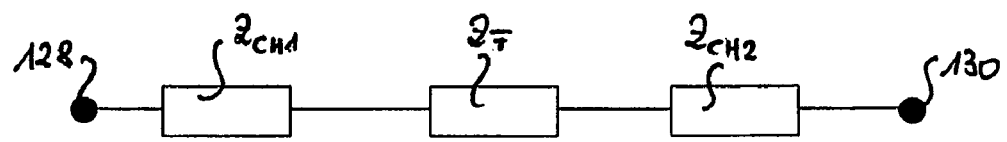
FIGS. 20 and 21 are illustrative substitute connection diagrams for embodiments of FIGS. 1 to 8.
Figure 21:
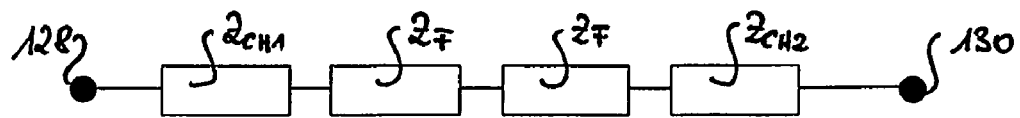

Two equations with two unknowns then exist for impedance relationships of the arrangements shown in FIGS. 20 and 21. The influence of the impedances $Z_{CH1}$, $Z_{CH2}$ and $Z_{CH3}$ and of the states and/or processes responsible for these impedances can be determined and taken into account in calculating the conductance.

Figure 22:
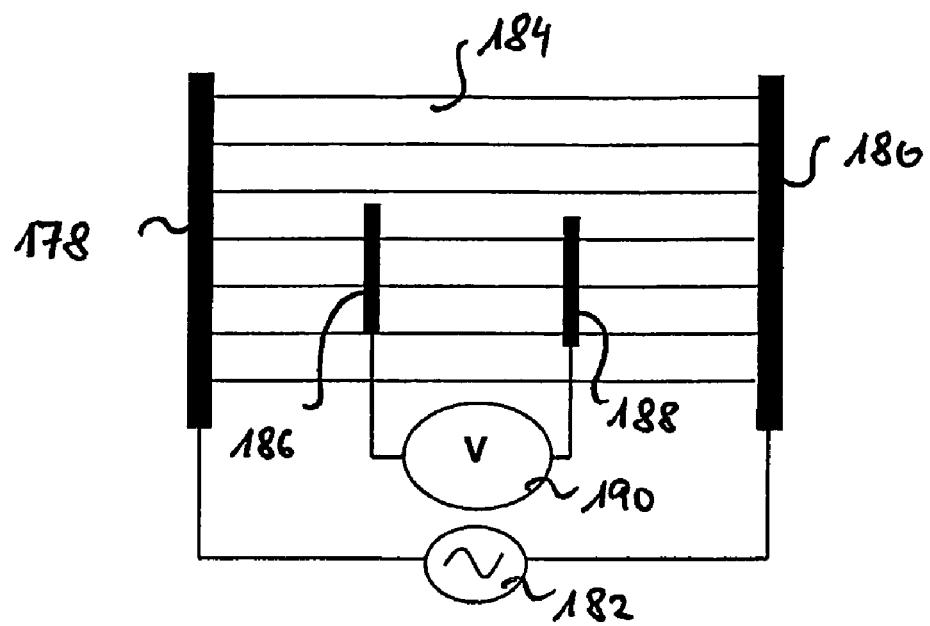
FIG. 22 is a known conductance electrode arrangement for a 4-pole conductance measurement.

Three conductance electrodes also allow a "slimmed-down four-pole measurement". Conventional four-pole conductance measurements employ, as illustrated in FIG. 22, two electrodes 178 and 180, which are connected to an electrical voltage source 182 and generate an almost homogeneous field 182. Two electrodes 186 and 188 are arranged in the field 184, which are connected to one another via an electrical voltage device 190 and are operated as passive electrodes for the conductance measurement.

Conventional arrangements involving four-pole conductance measurements have several disadvantages. In order to generate the field 184 the electrodes 178 and 180 have to be provided in the appropriate sizes. This leads not only to a correspondingly large manufacturing expenditure, but also requires a correspondingly large installation space. Furthermore the arrangement of the electrodes 186 and 188 relative to the electrodes 178 and 180 must be implemented accurately, so that a desired positioning of the electrodes relative to one another is achieved.

Figure 23:
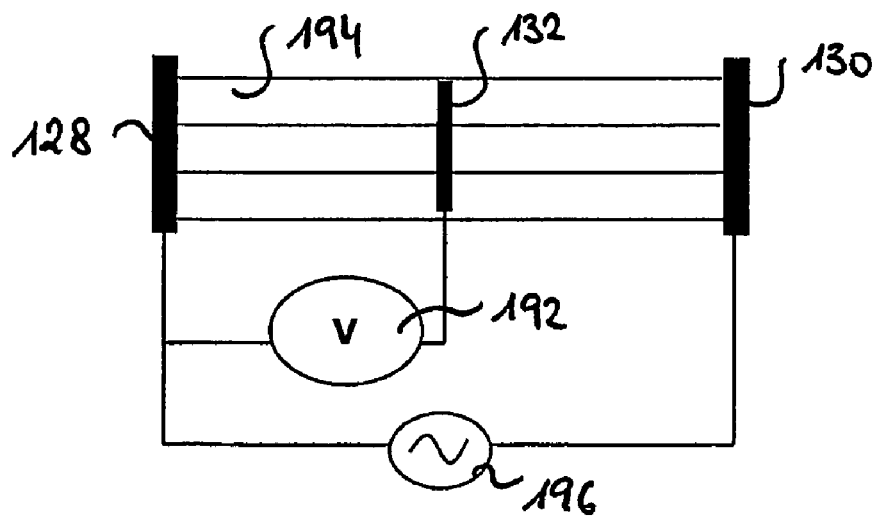
FIG. 23 is a conductance electrode arrangement for carrying out a preferred embodiment of the present invention in a "slimmed-down 4-pole conductance measurement"

On the other hand the present invention enables comparable measurements to be carried out with significantly smaller fields. This is illustrated in FIG. 23 for the electrodes 128, 130 and 132, where for the sake of simplicity the corresponding field line diaphragm devices are not shown. With the conductance electrodes 128 and 130 a homogeneous "narrow" field is produced, in which measurements can be carried out by means of the conductance electrode 132. For the "slimmed-down four-pole measurement" the conductance electrode 132 is connected to an electrical voltmeter 192, which in turn is connected to the conductance electrode 128. To generate a field 194, the conductance electrodes 128 and 130 are connected to an electrical voltage source 196. On account of the actions of the field 192 potential differences occur between the conductance electrodes 128 and 132, which can be detected by means of the voltmeter 192 and can be used to measure the electrical conductivity of a fluid. Alternatively, the conductance electrodes 132 and 130 may also be used for this purpose.

Embodiments are described hereinafter, with which statements can be made regarding the electrical conductivity of a fluid used for example for cleaning purposes in a washing machine or dishwasher. For this, a sensor arrangement with three conductance electrodes, as is illustrated for example in FIGS. 1 to 6, is employed.

The distance between conductance electrodes, the measurement frequency and the measurement voltages are used as parameters in this case. Statements regarding the electrical conductivity of a fluid may be made by carrying out measurements at least two different distances and/or at least two frequencies and/or at least two electrical voltages.

According to EN 27 888 "Determination of the electrical conductivity" the cell constant is given by the two-dimensional model:

$$K = s/(l \times d),$$

where K is the cell constant, s is the distance between two conductance electrodes used to measure the cell constant, d is the diameter of the conductance electrodes, and l is the length of the conductance electrodes.

Figure 24:
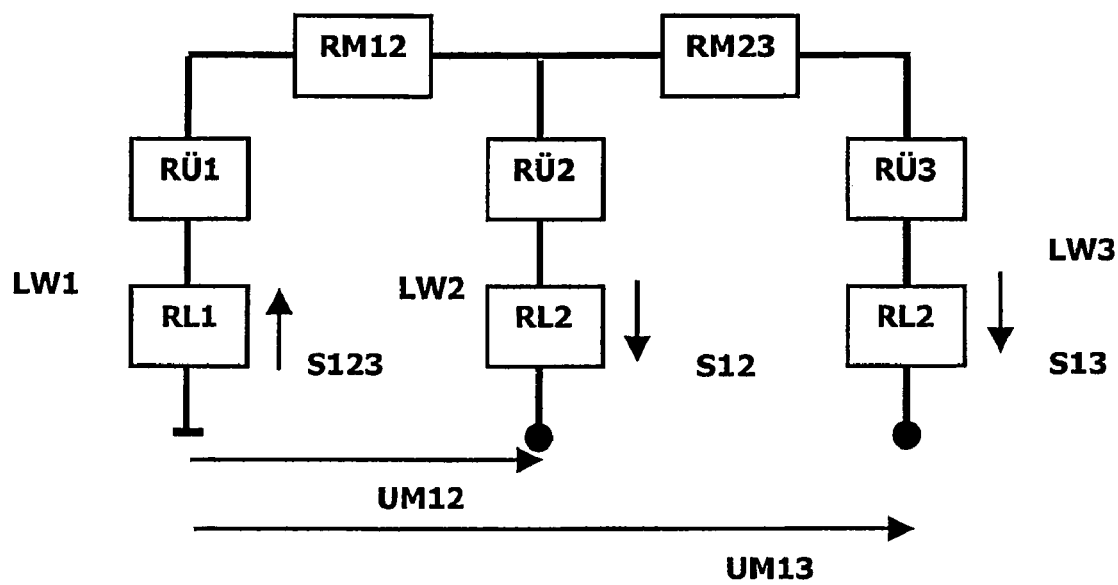
FIG. 24 is an illustrative substitute connection diagram for an embodiment according to the invention for determining the conductance.

FIG. 24 shows diagrammatically a substitute circuit diagram of a measurement arrangement with three conductance electrodes LW1, LW2 and LW3, which in the device shown in FIG. 1 may be provided by the conductance electrodes 128, 130 and 132. Resistances of the conductance electrodes LW1, LW2 and LW3 are denoted by the reference numerals RL1, RL2 and RL3.

Transition resistances from the individual conductance electrodes to the fluid or medium surrounding the measurement arrangement are denoted by the resistances RU1, RU2 and RU3. Resistances between conductance electrodes occurring on account of the fluid surrounding the measurement arrangement are denoted by resistances RM12 and RM23.

To assist in the understanding of the arrangement, it is proposed for the purposes of simplification to consider the connection of the conductance electrode LW1 is in this case as reference potential and for this purpose to connect it to earth for example.

In the measurements the potential differences UM12 and UM13 between the connection of the conductance electrode LW1 and the connection of the conductance electrode LW2 or the conductance electrode LW3 are measured, which are generated for example if the conductance electrodes LW2 and LW3 are supplied with power via one or more power sources (not shown). An electric current S123, which corresponds to the sum of the electric currents S12 and S13 flowing through the conductance electrodes LW2 and LW3, flows through the conductance electrode LW1. On account of the three conductance electrodes LW1, LW2 and LW3 used in this case, three different electrical cell constants exist, namely:

- an electrical cell constant with respect to the conductance electrodes LW1 and LW2
- an electrical cell constant with respect to the conductance electrodes LW1 and LW3
- an electrical cell constant with respect to the conductance electrodes LW2 and LW3
- an electrical cell constant with respect to the conductance electrode 1 on the one hand and the conductance electrodes LW2 and LW3, in the case of a bridged arrangement (i.e. the conductance electrodes LW2 and LW3 are connected to one another) on the other hand
- an electrical cell constant with respect to the conductance electrode 2 on the one hand and the conductance electrodes LW1 and LW3, in the case of a bridged arrangement, on the other hand
- an electrical cell constant with respect to the conductance electrode LW3 on the one hand and the conductance electrodes LW1 and LW2, in the case of a bridged arrangement, on the other hand.

In the following description it is assumed for the sake of simplification that the conductance electrodes LW1, LW2 and LW3 are of identical design and construction and are arranged "symmetrically" with respect to the conductance electrode LW2. Accordingly, it may be assumed for the sake of simplification that the resistances RL1, RL2 and RL3 are identical, the transition resistances RU1, RU2 and RU3 are identical, the resistances RM12 and RM23 are identical, the electrical cell constants with respect to the conductance electrodes LW1 and LW2 and with respect to the conductance electrodes LW2 and LW3 are identical, and the electrical cell constants with respect to the conductance electrode 1 and the bridged conductance electrodes LW2 and LW3 and with respect to the conductance electrode 3 and the bridged conductance electrodes LW1 and LW2 are identical.

In the following description the starting point is a simplified measurement, in which on the basis of the electric currents S12 and S13 information on the electrical conductivity is obtained and constant measurement voltages or currents, frequencies and wave forms of measurement voltage and current are used.

For the potential differences UM12 and UM13 existing between the connection of the conductance electrode LW1 and the connections of the conductance electrodes LW2 and LW3, the following relationships apply:

$$UM12 = S12 \times (RL1 + RU1 + RM12 + RU2 + RL2)$$

$$UM13 = S13 \times (RL1 + RU1 + RM12 + RM23 + RU3 + RL3)$$

On account of the structurally identical "symmetrical" measurement arrangement assumed in this case, it is furthermore true that:

RL1=RL2=RL3, which are hereinafter denoted as RL

RU1=RU2=RU3, which are hereinafter denoted as RU

RM12=RM23, which are hereinafter denoted as RM

UM12=UM13

From this we obtain the following equation for the ratio of the electric currents S12 and S13:

$$S12/S13 = (2 \times (RL + RU + RM))/(2 \times LW + 2 \times RU + RM)$$

With this implementation, statements can be made regarding the electrical conductivity of the fluid surrounding the measurement arrangement on the basis of measurements in which different distances exist between conductance electrodes, i.e. different electrical cell constants exist. This procedure furthermore enables for example ageing phenomena of the measurement arrangement, in particular of the conductance electrodes and temperature-dependent characteristics (e.g. temperature coefficients) of the measurement arrangement and in particular of the conductance electrodes as well as deposits thereon, to be compensated. For more accurate, more reliable statements regarding the electrical conductivity of the fluid, further measurements may be carried out in which different distance relationships apply.

On the basis of this, further statements can be made regarding the property of the fluid, as described hereinafter. Thus, in the case of the distance-based embodiment it is possible for example, from the ratio of measurement currents and the resulting statements regarding the electrical conductivity, to characterise at least partially field strength dependencies of constituents of the fluid surrounding the measurement arrangement.

Figure 25:
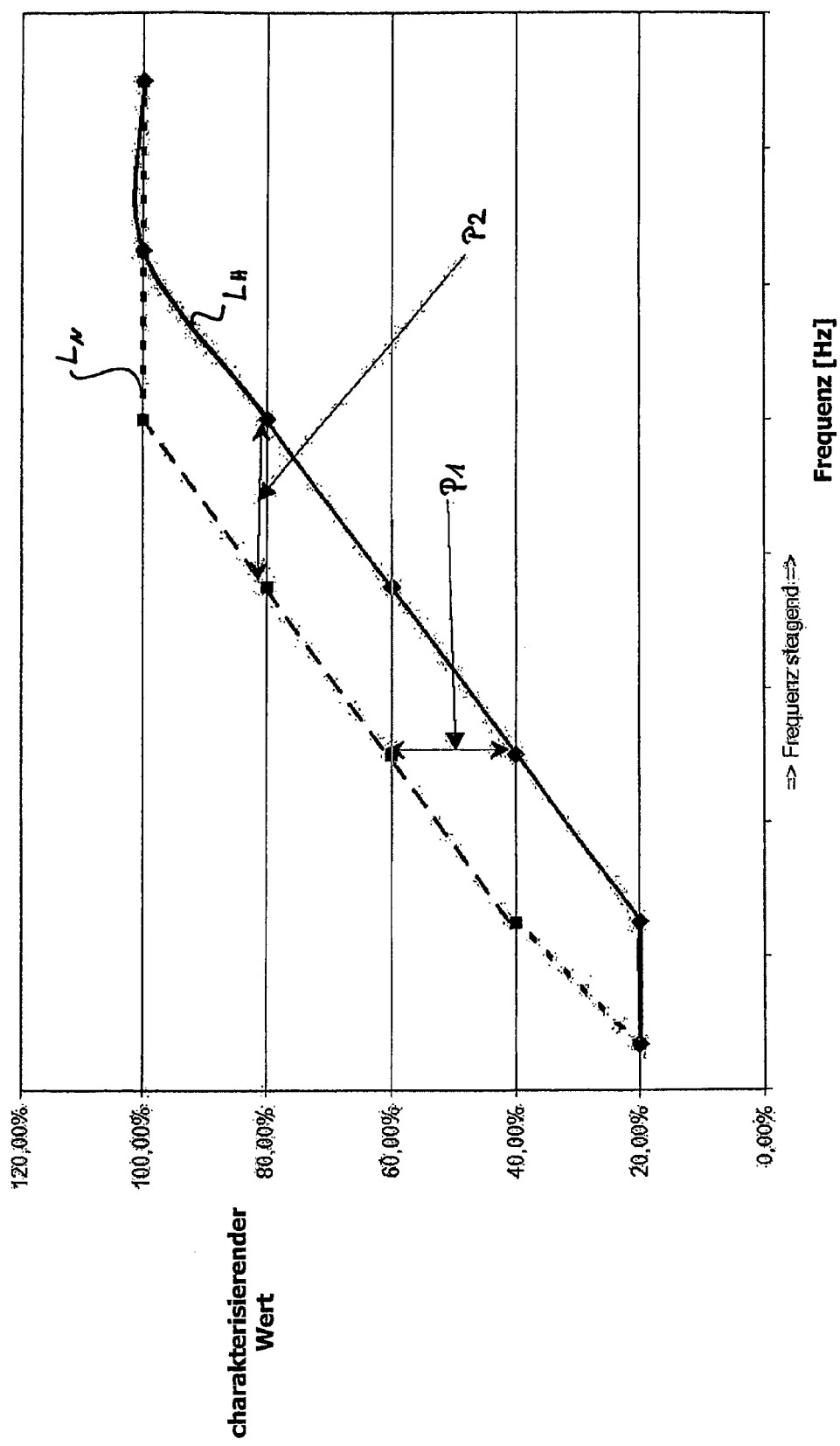
FIG. 25 is a diagram showing exemplary measurement results of an embodiment according to the invention for determining the conductance at different voltages and different frequencies.

FIG. 25 shows an idealised diagram of measurement results, in which the first parameter "frequency" was in each case varied for different values of the second parameter "voltage". The curve Lh reproduces frequency-dependent measurements at a high voltage, while the curve Ln reproduces frequency-dependent measurements at a lower voltage.

From these curves information can be obtained, as indicated for example by the arrow P1, on the fluid based on measurements at the same frequency but different voltages. The arrow P2 denotes an example in which statements can be made regarding the fluid at the same voltage but at different frequencies. On the basis of such measurement values it is possible for example in the case of a cleaning fluid to be monitored in a washing machine, to make statements regarding the detergent content and/or the type of detergent in the cleaning fluid. With measurement values at different frequencies statements can be made regarding mobility characteristics of constituents of the fluid surrounding the measurement arrangement. With measurement values at different voltages statements can be made regarding field strength dependencies of constituents of the fluid surrounding the measurement arrangement.

Figure 26:
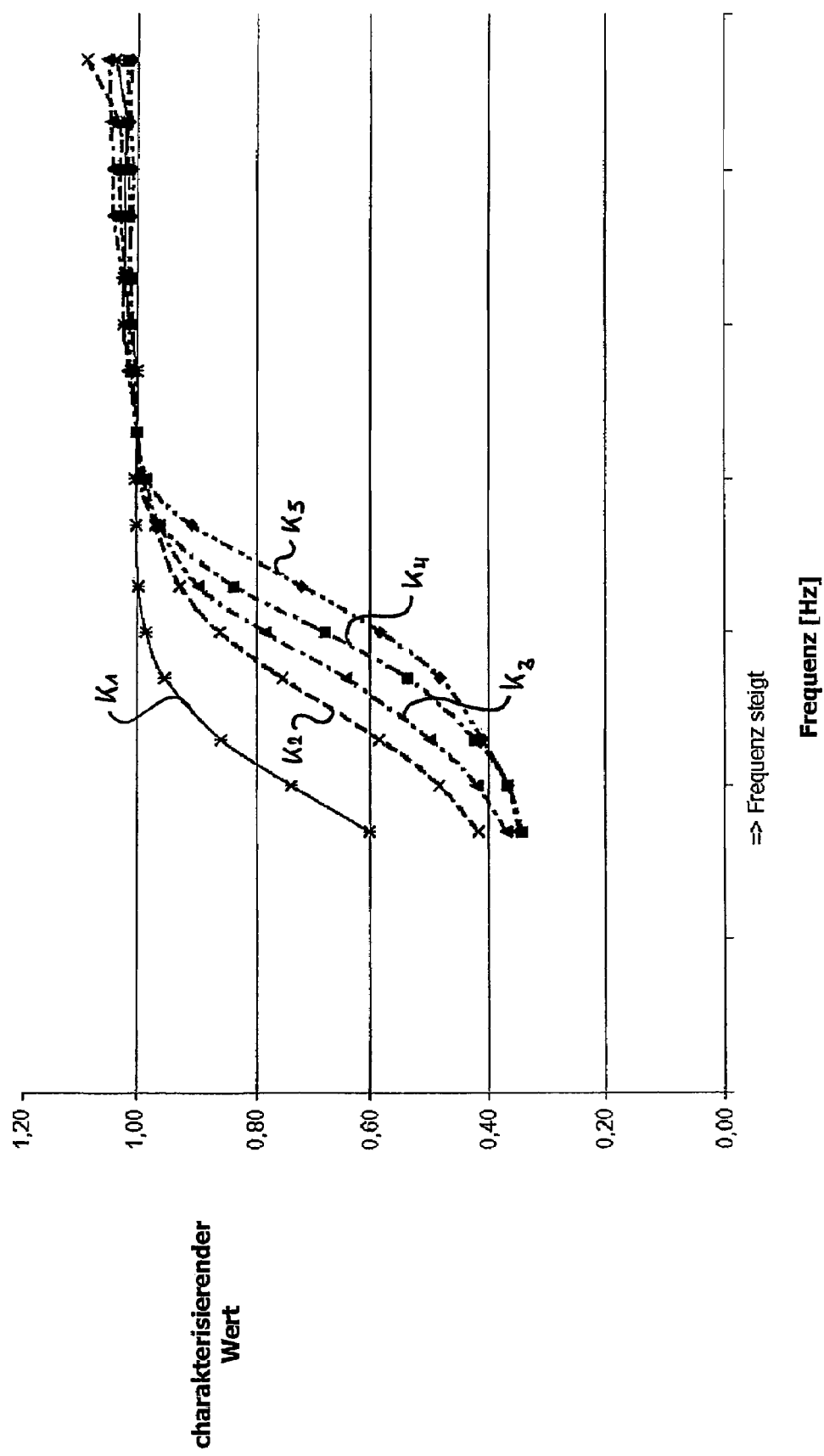
FIGS. 26 and 27 are diagrams showing exemplary measurement results of an embodiment according to the invention for determining the conductance at different frequencies and different fluid properties.
Figure 27:
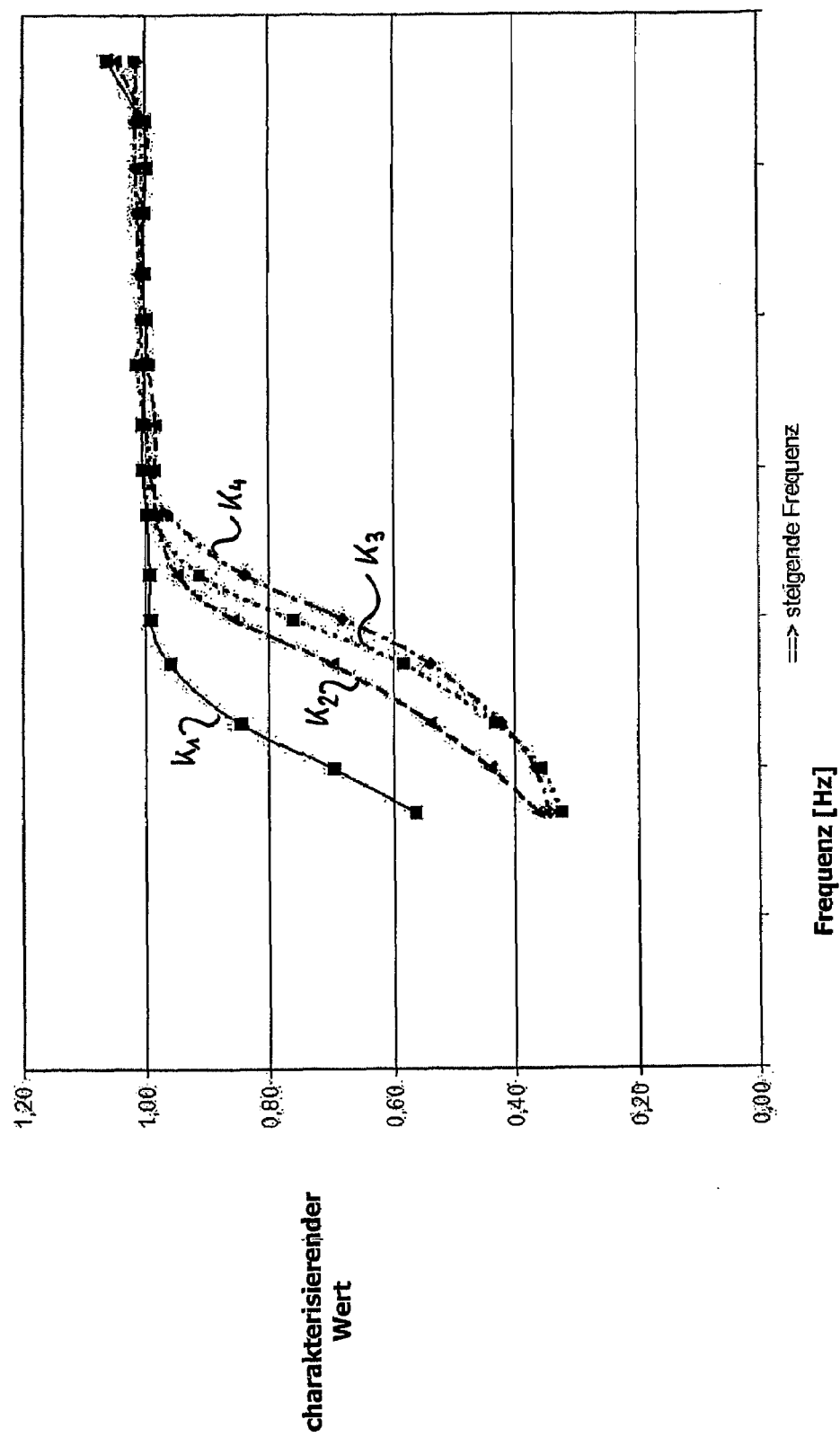

FIGS. 26 and 27 illustrate results of measurements for two values of the (first) parameter "voltage" at different values of the (second) parameter "frequency".

FIG. 26 shows five curves, which in each case represent characteristic values for the electrical conductivity, which are based on correlations of measurement values for a first and a second measurement voltage, at different frequencies. The curve K1 represents frequency-dependent characteristic values for the electrical conductivity at a concentration of a rinse agent used in a dishwasher of 0%. The curve K2 represents a rinse agent concentration of 25%, the curve K3 represents a rinse agent concentration of 50%, the curve K4 represents a rinse agent concentration of 100%, and the curve K5 represents a rinse agent concentration of 100%.

As can be seen in FIG. 26, the curves differ in their position relative to one another and in their shape. These differences can be used in order to obtain information on the rinse agent concentration in the fluid. It should be noted that it is not necessary to carry out so many measurements that a curve comparable to the curves shown in FIG. 26 is obtained. Instead, it may be sufficient to obtain at one frequency two measurement values for the first and second measurement voltages and derive therefrom a characteristic value.

FIG. 27 shows four curves, which in each case represent characterising values, based on correlation of measurement values for a first and a second measurement voltage, for the electrical conductivity of a cleaning fluid used in a dishwasher as a function of the frequency, for different types of rinse agent.

The curve K1 reproduces a commercially obtainable liquid rinse agent, curve K2 reproduces a rinse agent used as a reference, curve K3 reproduces a rinse agent in tablet form, and curve K4 reproduces a further reference rinse agent. Here too statements regarding the rinse agent can be made on the basis of the position and/or shape of the various curves or the position of individual characteristic values relative to one another, with respect to the electrical conductivities specified thereby.

Apart from the examples mentioned above for a first parameter, which can be used hereinafter as a second or third parameter, in particular wave forms of measurement currents and/or measurement voltages are envisaged.

If the first parameter has the parameter type "wave form", measurements of the electrical conductivity can be carried out with measurement voltages that for example have in one case a sine shape and in another case a saw-tooth shape, in one case a saw-tooth shape and in another case a rectangular shape, and so on.

Embodiments are described hereinafter, with which statements can be made concerning the fluid property optical turbidity. In this connection the starting point is a sensor arrangement involving the use of an optical transmitter and two optical receivers supplied by the transmitter, which provide two differently long optical measurement paths. Such arrangements are shown in FIGS. 1 to 6.

As physical variable, hereinafter reference is made for the sake of simplicity to the optical transmission of the fluid. Alternatively or in addition, provision is made to refer to the optical scattering and/or optical absorption of the fluid. In order to determine the optical scattering it is possible for example to use different measurement paths, one of which serves to detect optical measurement radiation propagating substantially rectilinearly, while the other serves to detect scattered measurement radiation. The optical absorption of the fluid can be determined for example by using measurement beams of different wavelengths, which may undergo different degrees of absorption on account of the different frequencies.

First of all an embodiment will be described in which two differently long optical measurement paths are used. Measurement results and initial variables of the optical measurement paths are denoted hereinafter by U, in which here and hereinafter the index "l" denotes a long measurement path and the index "k" denotes a short measurement path.

For purposes of standardisation initial variables Ulopt and Ukopt are used, which denote initial variables of the long and short measurement paths respectively if the corresponding optical measurement beams propagate (were to be propagated) through non-contaminated fluid (e.g. clear water). For the normalisation initial variables Ulopt and Ukopt obtained in the measurement are related to the respective optimal initial variable Ulopt and Ukopt respectively, in order to obtain standardised initial variables Ulnorm and Uknorm:

$$Ulnorm = Ul/Ulopt$$

$$Uknorm = Uk/Ukopt$$

By correlating the standardised initial variables, a turbidity factor T can be obtained as characterising value, in this case for example by forming the quotient:

$$T = Uknorm/Ulnorm$$

Receiver-side electric currents may for example be used as initial variables. A receiver-side current Ie may be given for example by:

$$Ie = Is \times Ku \times Ka$$

where

Ie denotes the receiver-side current,

Is denotes the transmitter-side current,

Ku denotes variables influencing the receiver-side current which are independent of the turbidity (here: in particular the optical transmission) of the fluid, and Ka denotes variables influencing the receiver-side current which are dependent on the turbidity (here: in particular the optical transmission) of the fluid.

Turbidity-independent variables Ku influencing the receiver-side current include for example ageing-related properties and changes in the transmitter and/or receiver and parameters of the optical measurement path (e.g. size and/or position of transmitter and/or receiver diaphragms, receiver-side and/or transmitter-side diaphragm characteristics, diameter of the optical measurement beam, deposits).

In order to determine a value T characterising the turbidity of the fluid, receiver-side currents (in the present example currents denoting optical transmissions) determined in the measurement are used as follows:

$$T = Iek/Iel = ((Isk \times Kuk \times Kmk)/(Isl \times Kul \times Kml))$$

In the measurement arrangement adopted here, the two receivers are supplied by the same transmitter, and accordingly for the sake of simplicity it may be assumed that:

$$Isk = Isl$$

Accordingly, the turbidity value T may be calculated according to the following equaton:

$$T = \text{const} \times (Kmk/Kml)$$

in which the constant "const." includes parameters independent of the turbidity.

Figure 28:
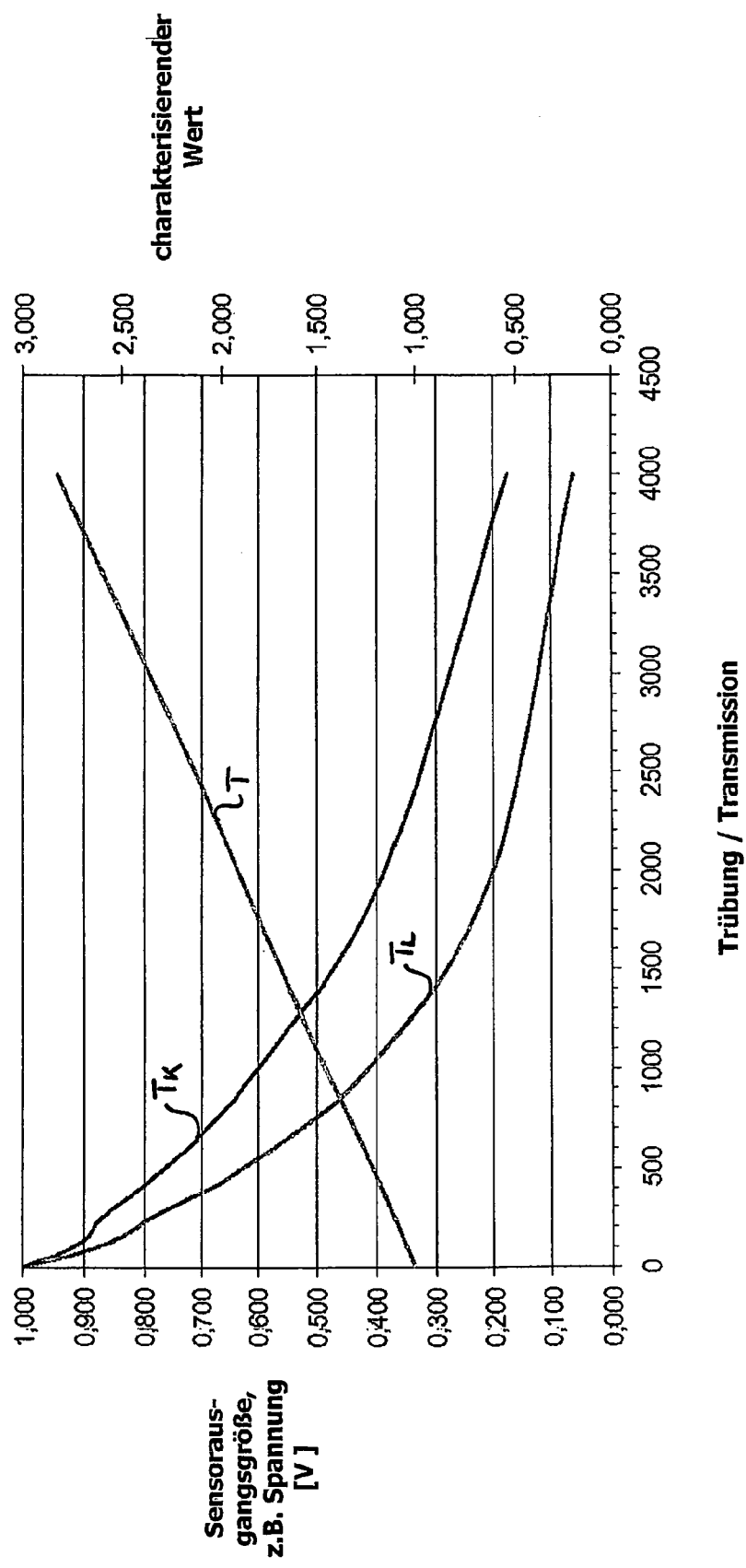
FIG. 28 is a diagram showing exemplary measurement results of an embodiment according to the invention for determining the turbidity and optical transmission.

FIG. 28 shows curves for different optical transmissions of a fluid (X axis) for a long measurement path (curve Ti) and a short measurement path (Tk), as well as a curve T which denotes the value T characterising the optical turbidity of the fluid.

As can be seen in FIG. 28, this embodiment leads to a substantially linear dependence for the values T. Statements concerning the fluid turbidity as well as changes in the latter can thus be obtained more easily. This also applies to statements concerning the fluid that are associated with its optical turbidity and/or can be derived therefrom (e.g. type of detergent or rinse agent, amount of detergent or rinse agent, gas or air bubbles in the fluid, effects caused by movement of the spray arm in a dishwasher, for example air bubbles, etc.) In addition such statements are also more reliable and accurate than hitherto, since on account of the correlation of different measurements results of the same physical variable, in this case the optical transmission, falsifying influences are compensated.

In another embodiment the optical turbidity is determined with a measurement beam at least two different frequencies, which here represent the physical variables. Hereinafter it is assumed for the sake of simplicity that an equally long measurement path is used for the measurements. This can be achieved if an optical measurement beam propagating between an optical transmitter and an optical receiver has the at least two predetermined frequencies at different times or in different time spans. It is also possible to use for each measurement beam its own optical receiver or plurality of optical receivers, one or more of which are appropriate for at least two optical measurement beams of different frequencies. In order to produce an optical measurement beam a dedicated transmitter or transmitters may furthermore be used for each measurement beam, which for example by using coloured filters emit two or more measurement beams of different frequencies.

In a comparable way to the above embodiments, in this case too it is advantageous to carry out a standardisation. Following this, receiver-side initial variables, which are generated in response to a reception of optical measurement beams of different frequencies can be correlated so as to calculate a value characterising the optical turbidity. In this case, on the basis of the characterising value statements may also be made concerning constituents and/or properties of the fluid that lead to a frequency-dependent turbidity. In this way statements may be made for example concerning gas bubbles or floating particles present in the fluid, and/or types and concentrations of detergent or rinse agent contained in the fluid.

In the following embodiment two differently long optical measurement paths are used, which differ in the respective receiver-side diaphragm characteristics. In this case the diaphragm characteristics are considered as the physical variable. For the sake of simplicity it is assumed in this case that there are no diaphragms on the transmitter side or that the transmitter-side diaphragms do not exert any influence. In the case of transmitter-side diaphragms in conjunction with or without receiver-side diaphragms the following details apply as appropriate. A diaphragm characteristic is understood to denote in particular the position and size of a diaphragm aperture relative to the receiver or to a measurement beam received by the receiver.

Initial variables of the optical measurement paths are denoted by U, the index "b1" denoting a first diaphragm characteristic and the index "b2" denoting a second diaphragm characteristic.

For purposes of standardisation initial variables Ub1opt and Ub2opt are used, which respectively denote initial variables of the measurement path with the diaphragm characteristic b1 and the measurement path with the diaphragm characteristic b2, when the corresponding optical measurement beams are propagated (would be propagated) through non-contaminated fluid (e.g. clear water). For the standardisation measured initial variables Ub1 and Ub2 are related to the respective optimal initial variables Ub1opt and Ub2opt, in order to obtain standardised initial variables Ub1norm and Ub2norm:

$$Ub1\text{norm} = Ub1/Ub1\text{opt}$$

$$Ub2\text{norm} = Ub2/Ub2\text{opt}$$

By correlating the standardised initial variables, a turbidity factor T may be determined as characteristic value, in this case for example by forming the quotient:

$$T = Ub2\text{norm}/Ub1\text{norm}$$

As initial variables of the optical measurement path there may be used for example receiver-side electrical measurement currents. A receiver-side current Ie may be given for example by:

$$Ie = Is \times Ku \times Ka$$

where
Ie denotes the receiver-side current,
Is denotes the transmitter-side current,
Ku denotes variables influencing the receiver-side current which are independent of the turbidity of the fluid, and
Ka denotes variables influencing the receiver-side current which are dependent on the turbidity of the fluid.

Turbidity-independent variables Ku influencing the receiver-side current include for example ageing-related properties and changes in the transmitter and/or receiver and further parameters of the optical measurement path.

To determine a value T characterising the turbidity of the fluid, receiver-side currents determined in a measurement may be employed as follows:

$$T = Iek/Iel = ((Isk \times KUb2 \times Kmk) \times (Isl \times KUb1 \times Kml))$$

In the measurement arrangement adopted here, the two receivers are supplied by the same transmitter, and accordingly it may be assumed for the sake of simplicity that:

$$Isk = Isl$$

Accordingly, the turbidity value T can be calculated according to the following equation:

$$T = \text{const.} \times (Kmk/Kml)$$

where the constant const. includes turbidity-dependent parameters.

Apart from the examples mentioned above, for a first parameter, which can be used hereinafter as second or third parameters, there are envisaged in particular wave forms of the optical measurement beam, measurement beam forms and intensities of optical measurement beams.

If the first parameter has the parameter type "wave form", measurements of the optical transmission can be carried out with a measurement beam which for example has in one case a sine shape, and in another case a saw-tooth shape, in one case a saw-tooth shape and in another case a rectangular shape, and so on.

With the parameter type "beam shape", measurement beams of different shape are generated. For example, it is possible to use for one measurement a diaphragm characteristic which generates a focussed measurement beam of small cross-section, while for another measurement a diaphragm characteristic is employed which leads to a measurement beam that propagates from the transmitter side to the receiver side. This allows for example statements concerning scattering effects in the fluid to be taken into account.

With measurement beams of different intensity, characteristics of a fluid and/or of particles contained in a fluid which for example have different absorption coefficients with respect to the measurement beam, can be taken into account.

Embodiments are described hereinafter, by means of which statements can be made concerning the temperature of a fluid used for example for cleaning in a washing machine or dishwasher, and variables associated therewith. In the following description a sensor arrangement is taken as the starting point, in which two temperature sensors are used that are arranged differently with respect to a fluid to be monitored, and in particular are spaced apart. Such an arrangement is shown for example in FIGS. 1 to 6.

Different thermal relationships or thermal transition resistances between the temperature sensors and their surroundings result from the above arrangement of temperature sensors (e.g. temperature sensors 124 and 126 in FIGS. 1 to 6).

In the arrangement adopted here, a first temperature sensor (e.g. temperature sensor 121 of FIGS. 1 to 6) is arranged projecting "far" into the fluid, and is separated from the latter basically only by a housing (e.g. housing 100 according to FIGS. 1 to 6 and thermally insulating paste possibly arranged therebetween).

In contrast to this a second temperature sensor (e.g. temperature sensor 126 according to FIGS. 1 to 6) is arranged so that in this case the thermal transition resistance is decisive as regards the surroundings of the measurement arrangement (e.g. the region lying to the left of the printed circuit board 142 in FIG. 1).

Moreover, the two temperature sensors are also thermally coupled.

The thermal coupling between the temperature sensors and the thermal coupling of the second temperature sensor with the surroundings are defined substantially by the measurement arrangement and the structure of a device (e.g. the devices according to FIGS. 1 to 6) comprising the temperature sensors.

Thus, for example, the thermal coupling between the two temperature sensors can be specified by their arrangement on a printed circuit board and/or by means of a thermally conducting paste arranged between the sensors.

The thermal coupling of the second temperature sensor to its surroundings may likewise be prescribed by a positioning on a printed circuit board and/or by means of thermally conducting paste.

Advantageously the thermal coupling between the second temperature sensor and its surroundings is worse than the thermal coupling between the two temperature sensors.

In contrast to this, the thermal coupling between the fluid and the first temperature sensor, projecting into the fluid, depends on the type of fluid and possibly also on the velocity of the fluid flowing past the first sensor or housing regions surrounding this.

The thermal capacity of the basic measurement arrangement is assumed to be constant.

Figure 29:
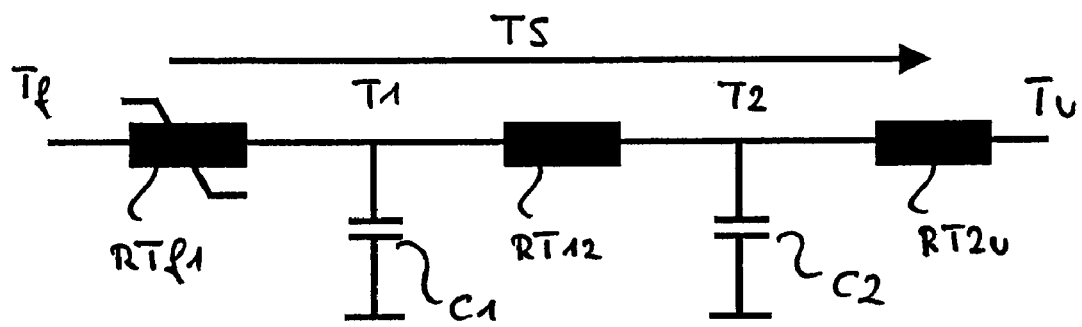
FIG. 29 is an illustrative substitute connection diagram for an embodiment according to the invention for measuring the temperature.

FIG. 29 shows an illustrative substitute circuit diagram for the circumstances mentioned above. The thermal capacity of the arrangement is denoted by the capacitors C1 and C2. The reference numeral Tf denotes the temperature of the fluid, the reference numeral T1 denotes the temperature detected by the first temperature sensor, the reference numeral T2 denotes the temperature detected by the second temperature sensor, and the reference numeral Tu denotes the temperature of the surroundings decisive for the second temperature sensor.

For a heat flow denoted by the reference numeral Ts, which propagates starting from the fluid via the temperature sensors to the surroundings, the following thermal transition resistances arise. A thermal transition resistance RTf1 is active starting from the fluid and continuing up to the first temperature sensor. This is followed by a more effective thermal transition resistance RT12 between the first and second temperature sensors. The thermal transition resistance between the second temperature sensor and the surroundings is denoted by the transition resistance RT2u.

A temperature measurement for a so-called static case is discussed hereinafter, in which it is assumed that the thermal transition resistance and the thermal coupling RTf1 between the fluid and the first temperature sensor is known. This knowledge can be obtained from the structure of the measurement arrangement and/or the nature of the household device in which the temperature measurement is to take place, and/or by relevant measurement methods. Advantageously the thermal transition resistance RTf1 is however obtained by the procedure described hereinafter with reference to a temperature measurement in a so-called dynamic case.

For the physical variable "temperature", the positions/arrangements of the temperature sensors are used here as first parameter. Since the positions/arrangements of the temperature sensors are also involved in the respective thermal couplings and thermal transition resistances, these too may be adopted as first parameter.

A static case is understood in particular to mean that the fluid does not move at least in the regions that are thermally coupled to the first temperature sensor. This may be achieved for example by not operating a fluid-conveying pump.

The heat flow TS propagating through the measurement arrangement may be defined as follows:

$$TS = (Tf - T1)/(RTf1)$$
$$= (T1 - T2)/(RT12)$$
$$= (T2 - Tu)/(RT2u)$$

in which, for the sake of simplicity, RT12 is assumed to be substantially constant, RT2u is assumed to be substantially constant, and RT2u is assumed to be substantially greater than RTf1. In addition, in the static case an at least substantially constant fluid temperature is assumed to be the case.

It is also assumed that RTf1 depends in particular on the velocity of the fluid relative to the first temperature sensor. This means that in this case one can start from a substantially constant RTf1, which is assumed to be known.

The temperature Tf of the fluid may thus be calculated as follows:

$$Tf=T1+(T1-T2)\times(RTf1/RT12)$$

In contrast to the static case, in the dynamic case the fluid moves at least in regions immediately adjacent to the first temperature sensor, or in regions which are (decisively) responsible for the thermal coupling between the fluid and the first temperature sensor. In household devices such as for example washing machines and dishwashers, cleaning fluids are generally held at appropriate temperatures depending on the actual operating states. The same is also true of the drying air used in dryers. Corresponding to this, in the dynamic case too an at least substantially constant temperature Tf of the fluid can be assumed.

The above details as regards the temperature measurement apply as appropriate to the dynamic case, if the thermal transition resistance between the fluid and the first temperature sensor for the dynamic case as a whole or for a quasi-stationary state is known. Irregular influences of fluid movements on the thermal coupling between the fluid and the first temperature sensor can be avoided by ensuring conditions for uniform fluid movements. A temperature measurement may be carried out for example if in the dynamic case the thermal coupling between the fluid and the first temperature sensor is known for a specific operating state of the household device and/or point in time and/or period of time, and the temperatures at the temperature sensors are then determined substantially accurately.

In this connection measurements of the temperature may be carried out so that, in the dynamic case, possible dynamic effects influencing temperature measurements are taken into account. For example, such effects can be taken into account or avoided if temperature measurements are carried out substantially simultaneously.

Here too the positions/arrangements of the temperature sensors, the respective thermal couplings and/or thermal transition resistances may be counted as first parameter.

By altering in a defined manner the relative velocity between the fluid and the first temperature sensor (e.g. by switching a fluid pump on and off in a controlled manner), transient effects as regards the measurement arrangement illustrated in FIG. 29 can be achieved. At the same time, as already mentioned, the temperature Tf of the fluid remains constant. The transition resistance RTf1 between the fluid and the first temperature sensor changes however on account of the movement of the fluid. As a result, at higher movement velocities of the fluid (fluid flow), higher temperatures are measured by the first temperature sensor compared to temperatures measured at lower fluid velocities. An increase in the fluid velocity leads to an increase in the temperature T1, while a reduction of the fluid velocity leads to a reduction of the temperature T1.

The thermal transition resistances RT12 and RT2u remain substantially constant. Since the thermal transition resistance RT2u is greater than the thermal transition resistance RTf1 and represents a dominating resistance in the substitute circuit diagram of FIG. 29, the heat flow TS basically does not change, or if so, only slightly. Corresponding to this, the thermal transition resistance RTf1 for the dynamic case (i.e. RTf1dyn) can be determined as follows, the index "stat" denoting variables in the static case and the index "dyn" denoting variables in the dynamic case:

$$RTf1\text{dyn}=(Tf-T1)\times(RT2u\text{stat}+RT12\text{stat})/(T1-Tu)$$

In order to illustrate the independence from the ambient temperature, the thermal transition resistance RTf1dyn may also be described as follows:

$$RTf1\text{dyn}=T1\text{stat}/T1\text{dyn}\times(RTf1\text{stat}+RT12\text{stat}+RT2u\text{stat})-(RT12\text{stat}+RT2u\text{stat})$$

In this connection it should be noted that the thermal transition resistance RTf1dyn is influenced by the fluid flow, whereas apart from the temperature T1dyn the further variables are substantially flow-independent and in particular the transition resistances can be fixed by the structure.

In this embodiment the thermal transition resistance RTf1dyn is counted as a physical variable, in which case here too the positions/arrangements of the temperature sensors, the respective thermal couplings and/or thermal transition resistances may be counted as first parameter.

The invention claimed is:

1. Method for the conductance-based determination of a property of a fluid employed in a household device comprising:
an arrangement of at least two conductance electrodes, characterised in that at least two representative measurement values for the conductivity of the fluid are obtained at different values of at least one measurement parameter, and at least one value characterising the property of the fluid is obtained by correlating the resultant measurement values, in which the measurement parameter is one of the following:
the frequency of an electrical measurement voltage or an electrical measurement current applied to at least one pair of electrodes of the electrode arrangement,
the waveform of such measurement voltage or such a measurement current,
the amplitude of such a measurement voltage or such a measurement current,
the position of a pair of electrodes of the electrode arrangement used for obtaining a measurement value,
the interspacing between two electrodes of the electrode arrangement used to obtain a measurement value,
the geometry of the conductance electrodes,
an operating state or a process variable of the household device.

2. Method according to claim 1, characterised in that at least two representative measurement values for the conductivity of the fluid are obtained at different values of each of at least two different measurement parameters, each of the measurement parameters being one of the following:
the frequency of an electrical measurement voltage or an electrical measurement current applied to at least one pair of electrodes of the electrode arrangement,
the wave form of such a measurement voltage or such a measurement current,
the amplitude of such a measurement voltage or such a measurement current,
the position of a pair of electrodes of the electrode arrangement used for obtaining a measurement value,
the interspacing between two electrodes of the electrode arrangement used to obtain a measurement value,
the geometry of the conductance electrodes, an operating state or a process variable of the household device.

3. Method according to claim 2, characterised in that for the measurement values the fluid impedance is measured between in each case two electrodes of the electrode arrangement.

4. Method according to claim 1, characterised in that for the measurement values of the fluid the fluid impedance is measured between in each case two electrodes of the electrode arrangement.

* * * * *